US008065010B2

(12) United States Patent
Brockway et al.

(10) Patent No.: US 8,065,010 B2
(45) Date of Patent: Nov. 22, 2011

(54) METHOD AND APPARATUS FOR MONITORING HEART FAILURE PATIENTS WITH CARDIOPULMONARY COMORBIDITIES

(75) Inventors: Marina V. Brockway, Shoreview, MN (US); Donald L. Hopper, Maple Grove, MN (US); Gerrard M. Carlson, Champlin, MN (US); Veerichetty Kadhiresan, Centerville, MN (US); Kenneth C. Beck, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 288 days.

(21) Appl. No.: 12/319,642

(22) Filed: Jan. 8, 2009

(65) Prior Publication Data

US 2009/0132000 A1    May 21, 2009

Related U.S. Application Data

(62) Division of application No. 10/897,856, filed on Jul. 23, 2004, now Pat. No. 7,480,528.

(51) Int. Cl.
*A61N 1/36* (2006.01)

(52) U.S. Cl. ............................ 607/42; 600/513; 600/529

(58) Field of Classification Search .................... 607/30, 607/42; 600/481, 483, 508, 510, 513, 529, 600/533, 536, 538, 543
See application file for complete search history.

(56) References Cited

U.S. PATENT DOCUMENTS

| 4,220,160 | A | 9/1980 | Kimball et al. |
|---|---|---|---|
| 4,428,380 | A | 1/1984 | Wong et al. |
| 4,586,514 | A | 5/1986 | Schlager et al. |
| 4,628,939 | A | 12/1986 | Little et al. |
| 4,702,253 | A | 10/1987 | Nappholz et al. |
| 4,796,639 | A | 1/1989 | Snow et al. |
| 4,905,706 | A | 3/1990 | Duff et al. |
| 4,967,760 | A | 11/1990 | Bennett et al. |
| 4,981,139 | A | 1/1991 | Pfohl |
| 5,003,976 | A | 4/1991 | Alt |
| 5,010,889 | A | 4/1991 | Bredesen et al. |

(Continued)

FOREIGN PATENT DOCUMENTS

JP        2004081854        3/2004

(Continued)

OTHER PUBLICATIONS

"U.S. Appl. No. 10/897,856 Advisory Action mailed Jun. 17, 2008", 3 pgs.

(Continued)

*Primary Examiner* — George R Evanisko
(74) *Attorney, Agent, or Firm* — Schwegman, Lundberg & Woessner, P.A.

(57) ABSTRACT

A system receives signals indicative of cardiopulmonary conditions sensed by a plurality of sensors and provides for monitoring and automated differential diagnosis of the cardiopulmonary conditions based on the signals. Cardiogenic pulmonary edema is detected based on one or more signals sensed by implantable sensors. If the cardiogenic pulmonary edema is not detected, obstructive pulmonary disease and restrictive pulmonary disease are each detected based on a forced vital capacity (FVC) parameter and a forced expiratory volume (FEV) parameter measured from a respiratory signal sensed by an implantable or non-implantable sensor. In one embodiment, an implantable medical device senses signals indicative of the cardiopulmonary conditions, and an external system detects the cardiopulmonary conditions based on these signals by executing an automatic detection algorithm.

20 Claims, 10 Drawing Sheets

U.S. PATENT DOCUMENTS

| | | | |
|---|---|---|---|
| 5,025,809 | A | 6/1991 | Johnson et al. |
| 5,074,303 | A | 12/1991 | Hauck |
| 5,179,947 | A | 1/1993 | Meyerson et al. |
| 5,218,969 | A | 6/1993 | Bredesen et al. |
| 5,301,679 | A | 4/1994 | Taylor |
| 5,337,752 | A | 8/1994 | Reeves |
| 5,554,177 | A | 9/1996 | Kieval et al. |
| 5,674,256 | A | 10/1997 | Carlson |
| 5,687,738 | A | 11/1997 | Shapiro et al. |
| 5,700,283 | A | 12/1997 | Salo |
| 5,792,195 | A | 8/1998 | Carlson et al. |
| 5,836,987 | A | 11/1998 | Baumann et al. |
| 5,860,933 | A | 1/1999 | Don Michael |
| 5,876,353 | A | 3/1999 | Riff |
| 5,935,081 | A | 8/1999 | Kadhiresan |
| 5,957,861 | A | 9/1999 | Combs et al. |
| 5,974,340 | A | 10/1999 | Kadhiresan |
| 6,002,777 | A | 12/1999 | Grasfield et al. |
| 6,044,294 | A | 3/2000 | Mortazavi et al. |
| 6,044,298 | A | 3/2000 | Salo et al. |
| 6,044,299 | A | 3/2000 | Nilsson |
| 6,058,329 | A | 5/2000 | Salo et al. |
| 6,076,015 | A | 6/2000 | Hartley et al. |
| 6,144,880 | A | 11/2000 | Ding et al. |
| 6,193,668 | B1 | 2/2001 | Chassaing et al. |
| 6,208,900 | B1 | 3/2001 | Ecker et al. |
| 6,223,064 | B1 | 4/2001 | Lynn et al. |
| 6,272,377 | B1 | 8/2001 | Sweeney et al. |
| 6,275,727 | B1 | 8/2001 | Hopper et al. |
| 6,351,673 | B1 | 2/2002 | Ding et al. |
| 6,360,127 | B1 | 3/2002 | Ding et al. |
| 6,409,675 | B1 | 6/2002 | Turcott |
| 6,411,840 | B1 | 6/2002 | Bardy |
| 6,418,342 | B1 | 7/2002 | Owen et al. |
| 6,459,929 | B1 | 10/2002 | Hopper et al. |
| 6,477,406 | B1 | 11/2002 | Turcott |
| 6,478,746 | B2 | 11/2002 | Chassaing et al. |
| 6,480,733 | B1 | 11/2002 | Turcott |
| 6,491,639 | B1 | 12/2002 | Turcott |
| 6,520,924 | B2 | 2/2003 | Lee |
| 6,527,729 | B1 | 3/2003 | Turcott |
| 6,542,775 | B2 | 4/2003 | Ding et al. |
| 6,561,986 | B2 | 5/2003 | Baura et al. |
| 6,575,916 | B2 | 6/2003 | Halleck et al. |
| 6,589,188 | B1 | 7/2003 | Street et al. |
| 6,626,842 | B2 | 9/2003 | Oka |
| 6,643,548 | B1 | 11/2003 | Mai et al. |
| 6,684,103 | B2 | 1/2004 | Ding et al. |
| 6,733,464 | B2 | 5/2004 | Olbrich et al. |
| 7,101,339 | B2 | 9/2006 | Daum et al. |
| 7,115,096 | B2 | 10/2006 | Siejko et al. |
| 7,139,609 | B1 | 11/2006 | Min et al. |
| 7,226,422 | B2 | 6/2007 | Hatlestad et al. |
| 7,480,528 | B2 | 1/2009 | Brockway et al. |
| 7,662,101 | B2 * | 2/2010 | Lee et al. .................. 600/484 |
| 2002/0072684 | A1 | 6/2002 | Stearns |
| 2002/0128563 | A1 | 9/2002 | Carlson et al. |
| 2002/0151938 | A1 | 10/2002 | Corbucci |
| 2003/0028221 | A1 | 2/2003 | Zhu et al. |
| 2003/0055461 | A1 | 3/2003 | Girouard et al. |
| 2003/0078624 | A1 | 4/2003 | Carlson et al. |
| 2003/0144702 | A1 | 7/2003 | Yu et al. |
| 2003/0144703 | A1 | 7/2003 | Yu et al. |
| 2003/0191503 | A1 | 10/2003 | Zhu et al. |
| 2003/0208240 | A1 | 11/2003 | Pastore et al. |
| 2003/0216664 | A1 | 11/2003 | Suarez |
| 2003/0233132 | A1 | 12/2003 | Pastore et al. |
| 2004/0039295 | A1 | 2/2004 | Olbrich et al. |
| 2004/0102712 | A1 | 5/2004 | Belalcazar et al. |
| 2004/0106960 | A1 | 6/2004 | Siejko et al. |
| 2004/0106961 | A1 | 6/2004 | Siejko et al. |
| 2004/0122484 | A1 | 6/2004 | Hatlestad et al. |
| 2004/0127792 | A1 | 7/2004 | Siejko et al. |
| 2005/0004609 | A1 | 1/2005 | Stahmann et al. |
| 2005/0065448 | A1 | 3/2005 | Stahmann et al. |
| 2005/0102001 | A1 | 5/2005 | Maile et al. |
| 2005/0148896 | A1 | 7/2005 | Siejko et al. |
| 2005/0149136 | A1 | 7/2005 | Siejko et al. |
| 2005/0256542 | A1 | 11/2005 | Pastore et al. |
| 2006/0020295 | A1 | 1/2006 | Brockway et al. |
| 2006/0030892 | A1 | 2/2006 | Kadhiresan et al. |
| 2007/0078491 | A1 | 4/2007 | Siejko et al. |
| 2009/0018461 | A1 | 1/2009 | Siejko et al. |

FOREIGN PATENT DOCUMENTS

| | | |
|---|---|---|
| JP | 2004082538 | 3/2004 |
| WO | WO-01/56651 A1 | 8/2001 |
| WO | WO-2004/012815 A1 | 2/2004 |
| WO | WO-2004/050178 A1 | 6/2004 |
| WO | WO-2005074361 A2 | 8/2005 |
| WO | WO-2006/028575 A2 | 3/2006 |

OTHER PUBLICATIONS

"U.S. Appl. No. 10/897,856, Response filed Mar. 4, 2008 to Final Office Action mailed Jan. 4, 2008", 24 pgs.

"U.S. Appl. No. 10/897,856 Non Final Office Action mailed Oct. 4, 2006", 15 pgs.

"U.S. Appl. No. 10/897,856 Response filed Jan. 2, 2007 to Non Final Office Action mailed Oct. 4, 2006", 24 pgs.

"U.S. Appl. No. 10/897,856, Final Office Action mailed Jan. 4, 2008", 16 pgs.

"BioZ® ICG Module", [onone]. [archived Jul. 1, 2001]. Retrieved from the Internet: <URL: http://web.archive.org/web/20010701105207/ http://www.cardiodynamics.com/cdprod50.html> 1 pg.

"BioZ.com™ Noninvasive Hemodynamic Monitor", [online]. [archived Jun. 17, 2000]. Retrieved from the Internet: <URL: http://web/archive.org/web/20000617081457/ http://www.cardiodynamics.com/cdprod10.html>, 2 pgs.

"CardioDynamics BioZtect™ ICG Sensor & Cable System", [online]. [archived Jul. 1, 2001]. Retrieved from the Internet: <URL: http://web.archive.org/web/200107011105810/http://www.cardiodynamics.com/cdprod60.html>, 2 pgs.

"CardioDynamics Company Overview", [online]. [archived Nov. 21, 2000]. Retrieved from the Internet: <URL: http://web.archive.org/web/20001121133300/ http://www.cardiodynamics.com/cdcomp10.html>, 2 pgs.

"European Application Serial No. 05806944.4, Office Action mailed Apr. 14, 2008", 8 pgs.

"European Application Serial No. 05806944.4, Response filed Oct. 17, 2008 to Office Action mailed Apr. 14, 2008", 22 pgs.

"International Search Report and Written Opinion for Application No. PCT/US2005/025235, date mailed Apr. 4, 2006", 20 pgs.

"Invitation to Pay Additional Fees and Partial Search Report for Application No. PCT/US2005/025235, date mailed Jan. 27, 2006", 9 pgs.

"Overview of Impedance Cardiography (ICG)", [online]. [archived Oct. 3, 2002]. Retrieved from the Internet: <URL: http:/web.archive.org/web/20021003000713/ http://www.impedancecariography.com/icgover10.html>, 5 pgs.

Aaron, S. D., et al., "How accurate is spirometry at predicting restrictive pulmonary impairment?", *Chest*, 115(3), (Mar. 1999), 869-873.

Brockway, M., et al., "Method and Apparatus for Optimization of Cardiac Resynchronization Therapy Using Heart Sounds", U.S. Appl. No. 10/865,498, filed Jun. 10, 2004, 45 pgs.

Ding, J., et al., "Cardiac Pacing Using Adjustable Atrio-Ventricular Delays", U.S. Appl. No. 10/008,830, filed Dec. 7, 2001, 42 pgs.

Ding, Jiang , et al., "Cardiac Pacing Using Adjustable Atrio-Ventricular Delays", U.S. Appl. No. 10/243,811, filed Sep. 13, 2002, 39 pgs.

Hatlestad, J. D., et al., "Physiological Response to Posture Change", U.S. Appl. No. 11/466,925, filed Aug. 24, 2006, 21 pgs.

Kadhiresan, V., et al., U.S. Appl. No. 10/914,632, filed Aug. 9, 2004, 18 pgs.

Kinderman, M., et al., "Optimizing the AV Delay in DDD Pacemaker Patients with High Degree AV Block: Mitral Valve Doppler Versus Impedance Cardiography", *PACE*, vol. 20, (Oct. 1997), 2453-2462.

Leonelli, F. M., et al., "Systolic and Diastolic Effects of Variable Atroventricular Delay and Patients with Complete Hear Block and Normal Ventricular Function", *Amer. J-Cardiology*, vol. 80, (Aug. 1, 1997),294-298.

Maile, K. R., et al., "A Dual-Use Sensor for Rate Responsive Pacing and Heart Sound Monitoring", U.S. Appl. No. 10/703,175, filed Nov. 6 2003, 41 pgs.

Maile, K. R., et al., "Determining a Patient's Posture From Mechanical Vibrations of the Heart", U.S. Appl. No. 10/900,570, filed Jul. 28, 2004, 24 pgs.

Ponikowski, P., et al., "Oscillatory Implications and Role of Augmented Peripheral Chemosensitivity", *Circulation*, 100, (1999), 2418-2424.

Ritter, P., et al., "New Method for Determining the Optimal Atrio-Ventricular Delay in Patients Place in DDD Mode for Complete Atrio-Ventricular Block", *NASPE Abstract #237*, (1995), p. 885.

Siejko, K. Z., "A Third Heart Sound Activity Index for Heart Failure Monitoring", U.S. Appl. No. 10/746,874, filed Dec. 24, 2003, 41 pgs.

Siejko Krzysztof Z., et al., "Method and Apparatus for Third Heart Sound Detection", U.S. Appl. No. 10/746,853, filed Dec. 24, 2003, 40 pgs.

Seijko, K. Z., et al., "Methods for Correction of Posture Dependence on Heart Sounds", U.S. Appl. No. 11/037,275, filed Jan. 18, 2005, 26 pgs.

Wariar, R., et al., "Systems and Methods for Multi-Axis Cardiac Vibration Measurements", U.S. Appl. No. 11/135,985, filed May 24, 2004.

Yu, Yinghong, et al., "Method and Apparatus for Optimizing Stroke Volume During DDD Resynchronization Therapy Using Adjustable Atrio-Ventricular Delays", U.S. Appl. No. 10/314,899, filed Dec. 9, 2002, 50 pgs.

Yu, Yinghong, et al., "Method and Apparatus for Optimizing Ventricular Synchrony During DDD Resynchronization Therapy Using Adjustable Atrio-Ventricular Delays", U.S. Appl. No. 10/314,910, filed Dec. 9, 2002, 50 pgs.

Zhang, Y., et al., "Ischemia Detection Using a Heart Sound Sensor", U.S. Appl. No. 11/148,107, filed Jun. 8, 2005, 41 pgs.

"European Application Serial No. 10173334.3, Extended European Search Report mailed Oct. 15, 2010", 10 pgs.

"Japanese Application Serial No. 2007-533593, Office Action mailed Dec. 27, 2010", 2 pgs.

Aaron, S. D, et al., "How accurate is spirometry at predicting restrictive pulmonary impairment?", Chest, 115(3), (Mar. 1999), 869-73.

"European Divisional Application Serial No. 10173334.3, Response filed May 23, 2011 to EP Search Report mailed Oct. 15, 2010", 8 pgs.

"Japanese Application Serial No. 2007-522593, Response filed Jun. 1, 2011 to Non Final Office Action mailed Dec. 27, 2010", 31 pgs.

"Japanese Application Serial No. 2007-522593, Notice of Allowance mailed Jun. 28, 2011", 3 pgs.

\* cited by examiner

METHOD AND APPARATUS FOR MONITORING HEART FAILURE PATIENTS WITH CARDIOPULMONARY COMORBIDITIES

CROSS-REFERENCE TO RELATED APPLICATIONS

This application is a divisional of U.S. application Ser. No. 10/897,856, filed Jul. 23, 2004, now issued as U.S. Pat. No. 7,480,528, which is hereby incorporated by reference in its entirety.

This application is related to co-pending, commonly assigned, U.S. patent application Ser. No. 10/612,387, "IMPLANTABLE DEVICES AND METHODS USING FREQUENCY-DOMAIN ANALYSIS OF THORACIC SIGNAL," filed Jul. 2, 2003, issued as U.S. Pat. No. 7,186,220, U.S. patent application Ser. No. 10/703,175, "DUAL-USE SENSOR FOR RATE RESPONSIVE PACING AND HEART SOUND MONITORING," filed Nov. 6, 2003, issued as U.S. Pat. No. 7,248,923, U.S. patent application Ser. No. 10/746,853, "METHOD AND APPARATUS FOR THIRD HEART SOUND DETECTION," filed on Dec. 24, 2003, issued as U.S. Pat. No. 7,431,699, and U.S. patent application Ser. No. 10/746,874, "A THIRD HEART SOUND ACTIVITY INDEX FOR HEART FAILURE MONITORING," filed on Dec. 24, 2003, issued as U.S. Pat. No. 7,115,096, which are hereby incorporated by reference in their entirety.

FIELD OF THE INVENTION

This document generally relates to patient monitoring systems and particularly, but not by way of limitation, to such systems monitoring treatment of heart failure patients with cardiopulmonary comorbidities.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. In a normal heart, the sinoatrial node, the heart's natural pacemaker, generates electrical impulses, known as action potentials, that propagate through an electrical conduction system to various regions of the heart to excite myocardial tissues in these regions. Coordinated delays in the propagations of the electrical impulses in a normal electrical conduction system cause the various regions of the heart to contract in synchrony such that the pumping functions are performed efficiently.

A blocked or otherwise damaged electrical conduction system causes irregular contractions of the myocardium, a condition generally known as arrhythmia. Arrhythmia reduces the heart's pumping efficiency and hence, diminishes the blood flow to the body. A weakened myocardium has decreased contractility, also resulting in diminished blood flow. A heart failure patient usually suffers from both a damaged electrical conduction system and a weakened myocardium. The diminished blood flow results in insufficient blood supply to various body organs, preventing these organs to function properly and causing various symptoms. For example, in a patient suffering decompensated heart failure, an insufficient blood supply to the kidneys results in abnormal fluid retention and increased central vascular pressure, and hence, cardiogenic pulmonary edema as well as edema in other organs.

Cardiogenic pulmonary edema shares common symptoms with pulmonary diseases such as obstructive pulmonary diseases including asthma and chronic obstructive pulmonary disease (COPD). Such common symptoms include difficulty of breathing, wheezing, and shortness of breathing. Safe and effective treatment for heart failure patients with cardiopulmonary comorbidities depends on differentiation of cardiogenic pulmonary edema from pulmonary diseases such as asthma and COPD. For example, beta-blockers (or beta-adrenergic blockers, pharmaceutical agents) are used to treat heart failure by reducing myocardial oxygen demand, resulting in improved cardiac functional status. However, beta-blockers are also known for their side effects including potential worsening of pulmonary conditions. Thus, heart failure patients who also suffer from asthma or COPD should be monitored while taking beta-blockers. While patient examinations in a doctor's office provide for the diagnosis of whether a heart failure patient also suffers asthma, biweekly titration of beta-blockers presents a challenge to an efficient and effective treatment.

For these and other reasons, there is a need for an efficient method and system to monitor the treatment of heart failure patients with cardiopulmonary comorbidities.

SUMMARY

A system receives signals indicative of cardiopulmonary conditions sensed by a plurality of sensors and provides for monitoring and automated differential diagnosis of the cardiopulmonary conditions based on the signals. The cardiopulmonary conditions include cardiogenic pulmonary edema and various pulmonary diseases.

In one embodiment, a system for detecting cardiopulmonary conditions includes a parameter input, a pulmonary edema detector, a low forced vital capacity (FVC) detector, and a pulmonary condition detector. The parameter input receives parameters indicative of a plurality of cardiopulmonary conditions. The parameters include an FVC parameter, a forced expiratory volume (FEV) parameter, and one or more edema-indicating parameters. The pulmonary edema detector detects cardiogenic pulmonary edema based on the one or more edema-indicating parameters. If the cardiogenic pulmonary edema is not detected, the low FVC detector detects a low FVC when the FVC parameter is below a predetermined threshold FVC parameter value. If the low FVC is detected, the pulmonary condition detector detects at least obstructive pulmonary disease and restrictive pulmonary disease based on the FVC parameter and the FEV parameter.

In one embodiment, a system includes an implantable medical device and an external system communicating with the implantable medical device via telemetry. The implantable medical device includes one or more sensors, an implant processor, and an implant telemetry module. The one or more sensors sense one or more signals indicative of a plurality of cardiopulmonary conditions. The implant processor processes the one or more signals. The implant telemetry module transmits the processed one or more signals to the external system. The external system includes an external telemetry module and an external processor. The external telemetry module receives the processed one or more signals. An external processor includes a cardiopulmonary condition detector that detects the plurality of cardiopulmonary conditions based on the processed one or more signals. The cardiopulmonary condition detector includes at least a cardiogenic pulmonary edema detector, an obstructive pulmonary disease detector, and a restrictive pulmonary disease detector.

In one embodiment, cardiopulmonary conditions are detected by executing an automatic detection algorithm using signals indicative of the cardiopulmonary conditions as inputs. According to the algorithm, cardiogenic pulmonary edema is detected based on at least one edema-indicating signal. An FVC parameter and an FEV parameter are measured from a respiratory signal. If the cardiogenic pulmonary edema is not detected, obstructive pulmonary disease and restrictive pulmonary disease are detected based on the measured FVC parameter and the measured FEV parameter.

In one embodiment, a method for monitoring cardiopulmonary conditions is provided. According to the method, signals indicative of a plurality of cardiopulmonary conditions are sensed using implantable sensors. Parameters are produced based on the signals. The plurality of cardiopulmonary conditions is detected based on the parameters. The plurality of cardiopulmonary conditions includes at least cardiogenic pulmonary edema, obstructive pulmonary disease, and restrictive pulmonary disease.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

The drawings illustrate generally, by way of example, but not by way of limitation, various embodiments discussed in the present document. The drawing are for illustrative purposes only and not to scale nor anatomically accurate.

DETAILED DESCRIPTION

Figure 1A:
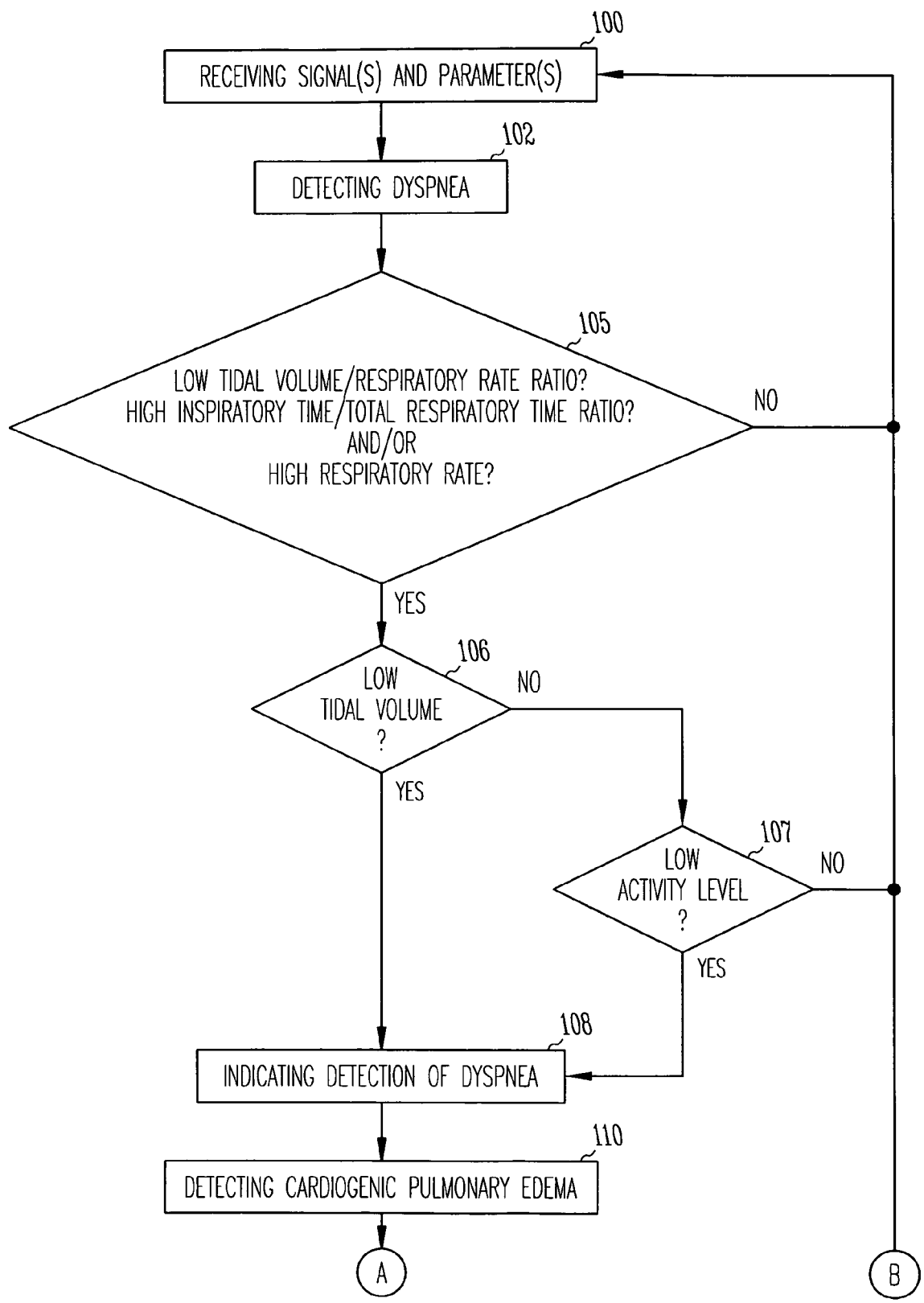
FIG. 1 is a flow chart illustrating one embodiment of a method for detecting cardiopulmonary conditions, including FIGS. 1A-C each showing portions of the flow chart.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a method and system for monitoring a heart failure patient with cardiopulmonary comorbidities using one or more implantable sensors incorporated into, or coupled to, an implantable medical device. The monitoring includes detection of the cardiopulmonary disorders by differential diagnoses based on sensed signals on a continuous or periodic basis. The result of the detection serves as a basis for making therapeutic decisions, such as starting, stopping, adjusting, and optimizing a therapy.

In this document, "cardiogenic pulmonary edema" refers to pulmonary edema resulted from heart failure and includes cardiogenic pulmonary edema or an indication of cardiogenic pulmonary edema.

In this document, a "user" includes a physician or other caregiver who examines and/or treats a patient using one or more of the methods and apparatuses discussed in the present document.

In this document, a "forced vital capacity (FVC) parameter" includes a parameter being a measure of the FVC, and a "forced expiratory volume (FEV) parameter" includes a parameter being a measure of the FEV. In one embodiment, the FVC parameter is a direct measure of the FVC, and the FEV parameter is a direct measure of the FEV. Such direct measures are obtained, for example, by measuring respiratory volumes using a spirometer. In another embodiment, the FVC parameter is an estimate of the FVC, and the FEV parameter is an estimate of the FEV. Such estimates are obtained, for example, by measurements performed on a thoracic impedance signal indicative of respiratory pattern and activities. In this embodiment, the FVC parameter is used to represent or indicate the FVC, and the FEV parameter is used to represent or indicate the FEV. In another embodiment, the FVC parameter and the FEV parameter are measured parameters providing for a calculation or estimation of an FVC-to-FEV ratio or an FEV-to-FVC ratio. In the description below, "FVC" includes an FVC or an FVC parameter, and "FEV" includes an FEV or an FEV parameter. The term "threshold FVC" includes a threshold FVC parameter value.

Figure 1B:
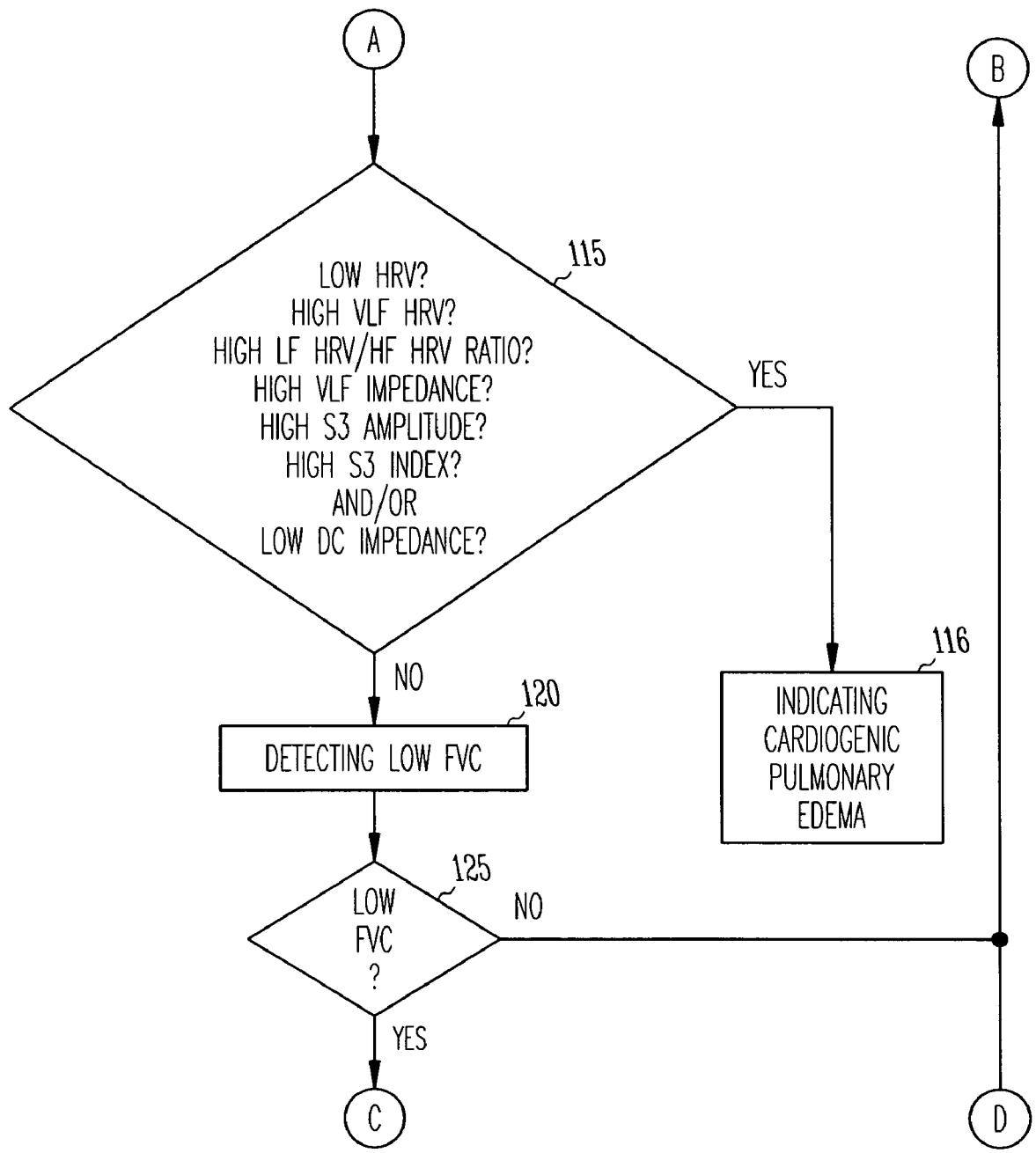
Figure 1C:
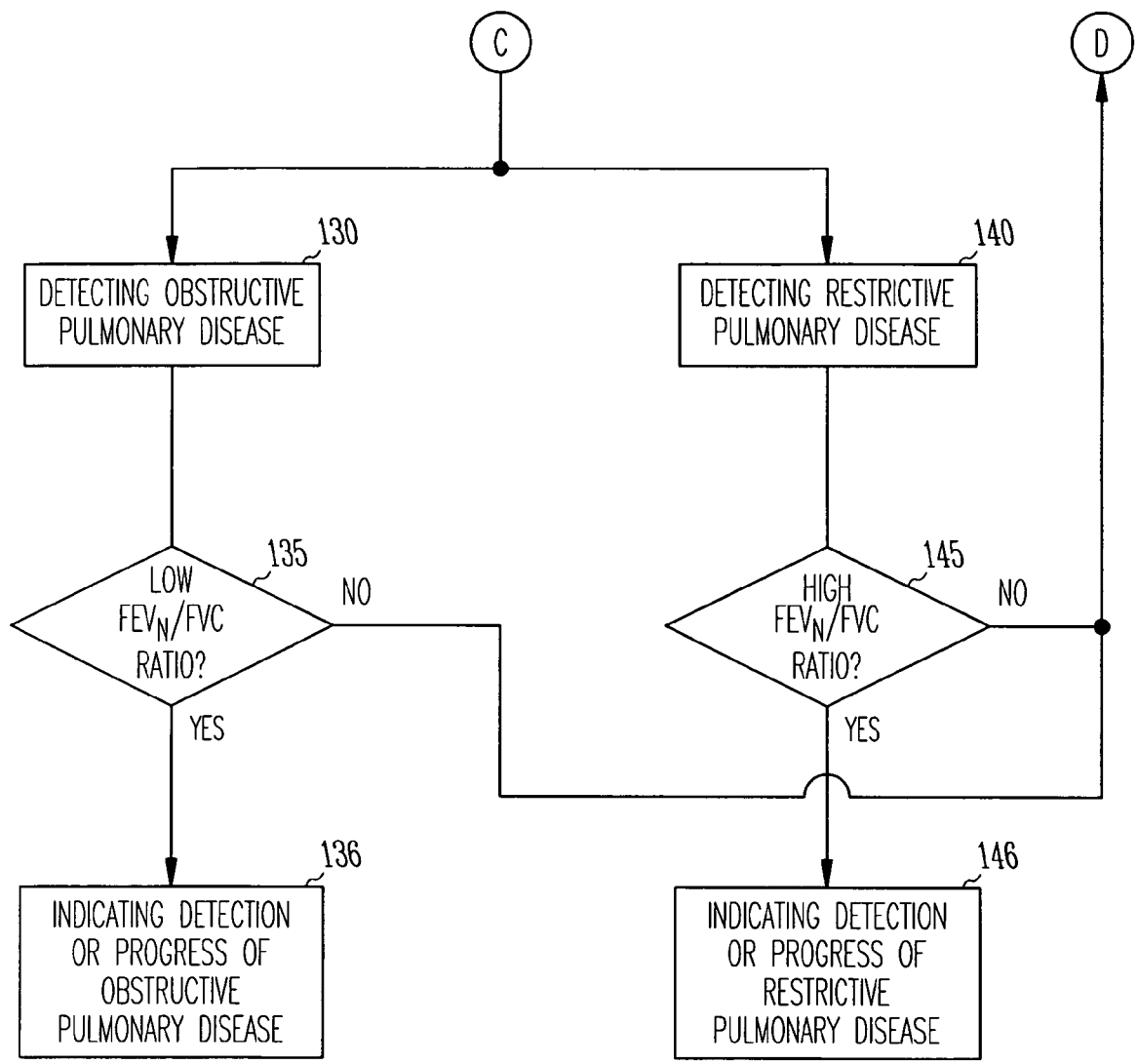

FIGS. 1A-C show a flow chart illustrating one embodiment of a method for detecting cardiopulmonary conditions. The method provides for detection of cardiogenic pulmonary edema, obstructive pulmonary disease, and restrictive pulmonary disease by a differential diagnostic process. In one embodiment, the method of FIGS. 1A-C is implemented as an automatic detection algorithm. In one specific embodiment, the automatic detection algorithm is executed by a combination of hardware and software of a computer-based system. In another specific embodiment, the automatic detection algorithm is implemented as a program executable by a computer or other computerized device. In one embodiment, the program is stored in a computer-readable medium to allow installation in computerized medical device systems. In one embodiment, the result of the execution of the automatic detection algorithm serves as a basis for making therapeutic decisions, such as to start, stop, adjust, and optimize a therapy. In a further embodiment, the therapy is optimized based on the result of the execution of the automatic detection algorithm on a continuous basis. In another further embodiment, the therapy is optimized based on the result of the execution of the automatic detection algorithm on a predetermined schedule, such as on a periodic basis. The therapy includes any therapy or combination of therapies treating one or more of the detected cardiopulmonary conditions, such as a drug therapy, an electrical therapy, a biological therapy, or any combination of these.

Signals and/or parameters indicative of the cardiopulmonary conditions are received at 100. In one embodiment, the signals are sensed by implantable sensors. In one further embodiment, the implantable sensors are connected to or included in an implantable medical device. The parameters are derived from the signals for the detection of the cardiopulmonary conditions.

Dyspnea is to be detected at 102. In one embodiment, dyspnea is detected based on a respiratory signal and an activity signal. The respiratory signal, such as an impedance signal sensed by an implantable impedance sensor, indicates a patient's lung volume, which changes cyclically with respiratory cycles (breaths) and hence the respiratory pattern. In one embodiment, the respiratory signal is a minute-ventilation (MV) impedance signal that is a processed thoracic impedance signal indicative tidal volume and respiratory rate. MV is the product of the tidal volume (air expired during each respiratory cycle) and respiratory rate (number of respiratory cycles per minute). The thoracic impedance signal is sensed by the implantable impedance sensor. The activity signal, such as an acceleration signal sensed by an implantable accelerometer, indicates the patient's gross physical activity level. Dyspnea is detected when the respiratory signal indicates rapid and shallow breath and the activity signal indicates that the rapid and shallow breath is substantially unrelated to the patient's physical activity. In one embodiment, to detect dyspnea, one or more of a low tidal-volume/respiratory-rate ratio, a high inspiratory-time/total-respiratory-time ratio, and a high respiratory rate are detected at 105. The tidal volume is measured from the respiratory signal as the volume of the air expired during each respiratory cycle. The respiratory rate is calculated from the number of respiratory cycles per minute, as shown in the respiratory signal. The low tidal-volume/respiratory-rate ratio is detected when a measured tidal-volume/respiratory-rate ratio is below a predetermined threshold ratio. The inspiratory time is measured from the respiratory signal as the time interval of the inspiratory phase of the respiratory cycle. The expiratory time is measured from the respiratory signal as the time interval of the expiratory phase of the respiratory cycle. The high inspiratory-time/total-respiratory-time ratio, also referred to as the high inspiration/expiration ratio, is detected when the inspiratory-time/total-respiratory-time ratio exceeds a predetermined threshold ratio. The high respiratory rate is detected when the measured respiratory rate exceeds a predetermined threshold rate. If a detection of at least one of these conditions is indicated at 105, a low tidal volume is to be detected at 106 by comparing the measured tidal volume to a predetermined threshold tidal volume. If a detection of the low tidal volume is indicated at 106, a detection of dyspnea is indicated at 108. If no detection of the low tidal volume is indicated at 106, a low activity level is to be detected at 107. The low activity level is detected when the patient's gross physical activity level, as indicated by the activity signal, is below a predetermined threshold level representing a resting state. If a detection of the low activity level is indicated at 107, which indicates that the patient is substantially inactive, a detection of dyspnea is indicated at 108.

In another embodiment, dyspnea is detected by receiving a command triggering the process of detecting the cardiopulmonary conditions. For example, the command is entered by the patient based on his/her physical feeling or by another person observing or examining the patient. In one embodiment, dyspnea is detected either automatically based on the respiratory signal and/or the activity signal, as discussed above, or by a person based on feeling or observation.

If the detection of dyspnea is indicated at 108, cardiogenic pulmonary edema is to be detected at 110. In one embodiment, cardiogenic pulmonary edema is detected based on one or more signals sensed by the implantable sensors. The one or more signals each indicate one or more cardiopulmonary conditions. In a further embodiment, cardiogenic pulmonary edema is detected based on one or more parameters each produced based on the one or more signals sensed by the implantable sensors. In one specific embodiment, cardiogenic pulmonary edema is detected by detecting a low heart rate variability (HRV), i.e., when a measured HRV is lower than a predetermined threshold HRV, or when a decrease in the measured HRV exceeds a predetermined margin, at 115. In another specific embodiment, cardiogenic pulmonary edema is detected by detecting a high very-low-frequency (VLF) HRV, i.e., when a measured VLF HRV is higher than a predetermined threshold VLF HRV, at 115. The VLF HRV includes components of the HRV having frequencies between about 0.0033 Hz and 0.04 Hz. A high VLF HRV is suggestive of periodic breathing. In another specific embodiment, cardiogenic pulmonary edema is detected by detecting a high ratio of low-frequency (LF) HRV to high-frequency (HF) HRV, i.e., when the LF-HRV/HF-HRV ratio exceeds a predetermined threshold ratio, at 115. The LF HRV includes components of the HRV having frequencies between about 0.04 Hz and 0.15 Hz. The HF HRV includes components of the HRV having frequencies between about 0.15 Hz and 0.40 Hz. The LF-HRV/HF-HRV ratio is used to track trends in shifts of autonomic balance. A substantial change in the LF-HRV/HF-HRV ratio indicates a change in systemic stress that indicates the degree to which the sympathetic nervous system is over-stimulated. In another specific embodiment, cardiogenic pulmonary edema is detected by detecting a high very-low-frequency (VLF) impedance, i.e., when a VLF impedance exceeds a predetermined threshold VLF impedance, at 115. The VLF impedance includes VLF components of a thoracic impedance signal sensed by an implantable impedance sensor and suggests periodic breathing. The VLF components are within a frequency range of about 0.0033 Hz to 0.016 Hz. In another specific embodiment, cardiogenic pulmonary edema is detected by detecting a high third heart sound (S3) amplitude, i.e., when the S3 amplitude exceeds a predetermined threshold amplitude, at 115. A substantial presence of S3 indicates heart failure. In another specific embodiment, cardiogenic pulmonary edema is detected by detecting an S3 index, i.e., when the S3 index exceeds a predetermined threshold level, at 115. The S3 index is a ratio, or an estimate of the ratio, of the number of S3 beats to the number of all heart beats, where the S3 beats are each a heart beat during which an occurrence of S3 is detected. It is a measure of a frequency of S3 presence used to indicate heart failure. In another specific embodiment, cardiogenic pulmonary edema is detected by detecting a direct-current (DC) impedance, i.e., when the DC impedance is below a predetermined threshold DC impedance, at 115. The DC impedance includes DC (and/or ultra-low-frequency) components of the thoracic impedance signal sensed by the implantable impedance sensor and indicates a lung fluid status. In one embodiment, cardiogenic pulmonary edema is detected by detecting one of the low HRV, the high VLF HRV, the high LF-HRV/HF-HRV ratio, the high VLF impedance, the high S3 amplitude, the high S3 index, and the low DC impedance. A detection of cardiogenic pulmonary edema is indicated at 116 after the one of these conditions is detected at 115. In another embodiment, cardiogenic pulmonary edema is detected by detecting two or more of the low HRV, the high VLF HRV, the high LF-HRV/HF-HRV ratio, the high VLF impedance, the high S3 amplitude, the high S3 index, and the low DC impedance at 115. In one specific embodiment, a unanimous or majority voting determines whether to indicate a detection of cardiogenic pulmonary edema at 116. In one specific embodiment, a weighted voting determines whether to indicate a detection of cardiogenic pulmonary edema at 116. A weighing coefficient is assigned to each of the conditions including the low HRV, the high VLF HRV, the high LF-HRV/HF-HRV ratio, the high VLF impedance, the high S3 amplitude, the high S3 index, and the low DC impedance. The detection of each of these conditions is given a predetermined weight in the voting.

If cardiogenic pulmonary edema is not detected at 115, a low FVC is to be detected at 120. The low FVC is detected when a measured FVC is less than a predetermined threshold FVC. In one embodiment, the FVC is measured from a spirometry signal. In another embodiment, the FVC is measured from a respiratory signal sensed by an implantable sensor, such as the MV impedance signal.

If the low FVC is detected at 125, obstructive pulmonary disease is to be detected at 130, and restrictive pulmonary disease is to be detected at 140. Obstructive pulmonary disease is detected by detecting a low $FEV_N/FVC$ ratio, i.e., when the ratio of the measured $FEV_N$ (where N denotes that the FEV is measured at N seconds after the expiration phase of a respiratory cycle starts) to the measured FVC falls below a predetermined obstructive pulmonary disease threshold ratio at 135. In one embodiment, the FVC and the $FEV_N$ are both measured from the spirometry signal. In another embodiment, the FVC and the $FEV_N$ are both measured from measured from the respiratory signal sensed by the implantable sensor, such as the MV impedance signal. If the low $FEV_N/FVC$ ratio is detected at 135, a detection of obstructive disease is indicated at 136. In one embodiment, the restrictive pulmonary disease is detected by detecting a high $FEV_N/FVC$ ratio, i.e., when the ratio of the measured $FEV_N$ to the measured FVC exceeds a predetermined restrictive pulmonary disease threshold ratio at 145. If the high $FEV_N/FVC$ ratio is detected at 145, a detection of restrictive pulmonary disease is indicated at 146.

One or more of the thresholds used in the detection of dyspnea, cardiogenic pulmonary edema, low FVC, obstructive pulmonary disease, and restrictive pulmonary disease as described above with reference to steps 105, 106, 107, 115, 125, 135, and 145 are individually established and adjusted for each patient. In one embodiment, all the thresholds are established based on baseline data collected when the system is initially used with a patient and when the patient is in a stable condition. The baseline data represent the patient's baseline condition, which is used as a reference for future progress of the conditions. In one embodiment, one or more of the thresholds are verified periodically when a patient is known to be in a stable condition and adjusted when appropriate.

Figure 2A:
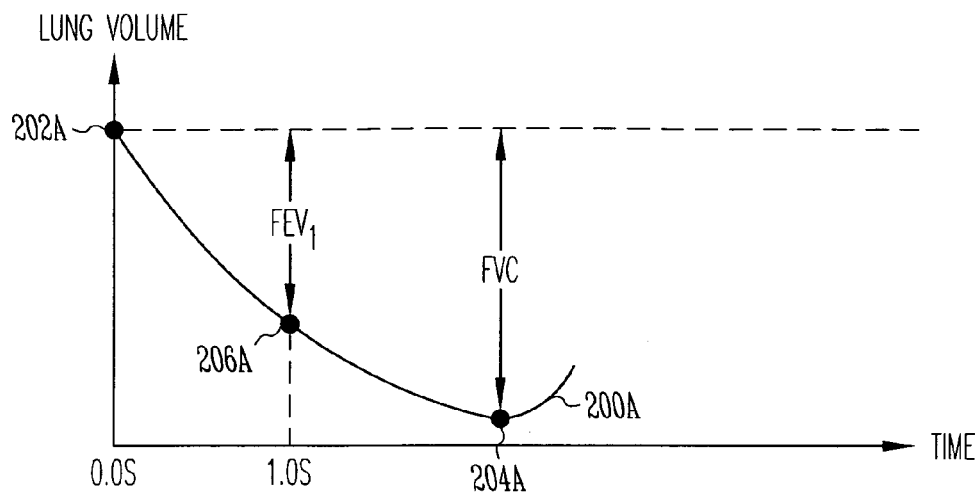
FIG. 2A is a graph illustrating a respiratory signal indicative of normal pulmonary function.
Figure 2B:
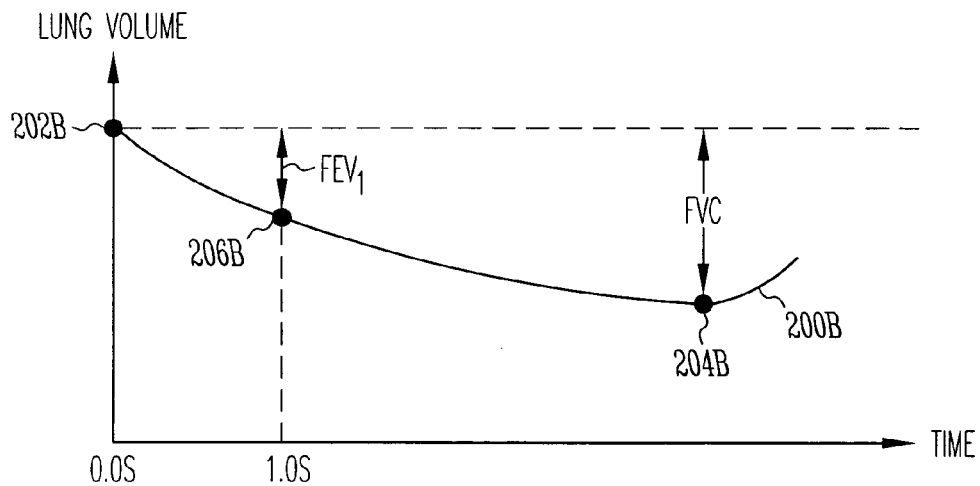
FIG. 2B is a graph illustrating a respiratory signal indicative of obstructive pulmonary diseases.
Figure 2C:
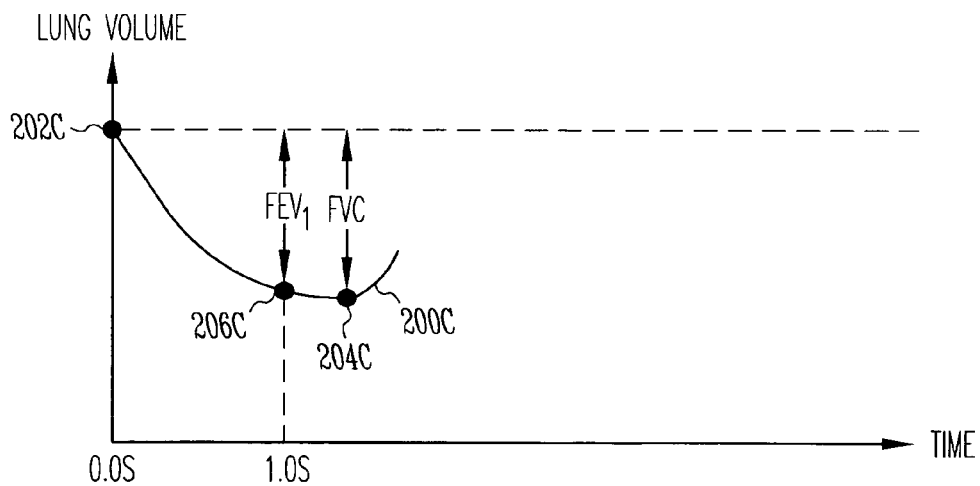
FIG. 2C is a graph illustrating a respiratory signal indicative of restrictive pulmonary diseases.

FIGS. 2A-C illustrate the measurement of the FVC and $FEV_N$. FIG. 2A is a graph illustrating a respiratory signal 200A indicative of normal pulmonary function. FIG. 2B is a graph illustrating a respiratory signal 200B indicative of a respiratory pattern seen in an obstructive pulmonary disease. FIG. 2C is a graph illustrating a respiratory signal 200C indicative of a respiratory pattern seen in a restrictive pulmonary disease. In FIGS. 2A-C, the respiratory signals are each a signal indicative of lung volume, which changes cyclically with the respiration cycles and shows the respiratory pattern. In one embodiment, respiratory signals 200A-C are spirometry signals sensed by a spirometer. In another embodiment, respiratory signals 200A-C are respiratory signals sensed by an implantable sensor, such as the MV impedance signal sensed by the implantable impedance sensor. The FVC is measured as the change of the lung volume from the beginning of the expiratory phase to the beginning of the inspiratory phase in a respiratory cycle. As illustrated in FIGS. 2A-C, the FVC for respiratory signal 200A is measured as the change in lung volume between points 202A and 204A; the FVC for respiratory signal 200B is measured as the change in the lung volume between points 202B and 204B; and the FVC for respiratory signal 200C is measured as the change in the lung volume between points 202C and 204C. The $FEV_N$ is measured as the change in the lung volume over a predetermined time interval (N seconds) starting with the beginning of the expiratory phase. In one specific embodiment, as illustrated in FIGS. 2A-C, the predetermined time interval is 1.0 second, and $FEV_1$ is measured. The $FEV_1$ for respiratory signal 200A is measured as the change in the lung volume between points 202A and 206A; the $FEV_1$ for respiratory signal 200B is measured as the change in the lung volume between points 202B and 206B; and the $FEV_1$ for respiratory signal 200C is measured as the change in the lung volume between points 202C and 206C. In other embodiments, the $FEV_N$ are measured at other times such as 3 or 6 seconds after the beginning of the respiratory cycle (i.e., $FEV_3$ or $FEV_6$), and the thresholds for detecting the high $FEV_N/FVC$ ratio and the low $FEV_N/FVC$ ratio are adjusted accordingly.

Figure 3:
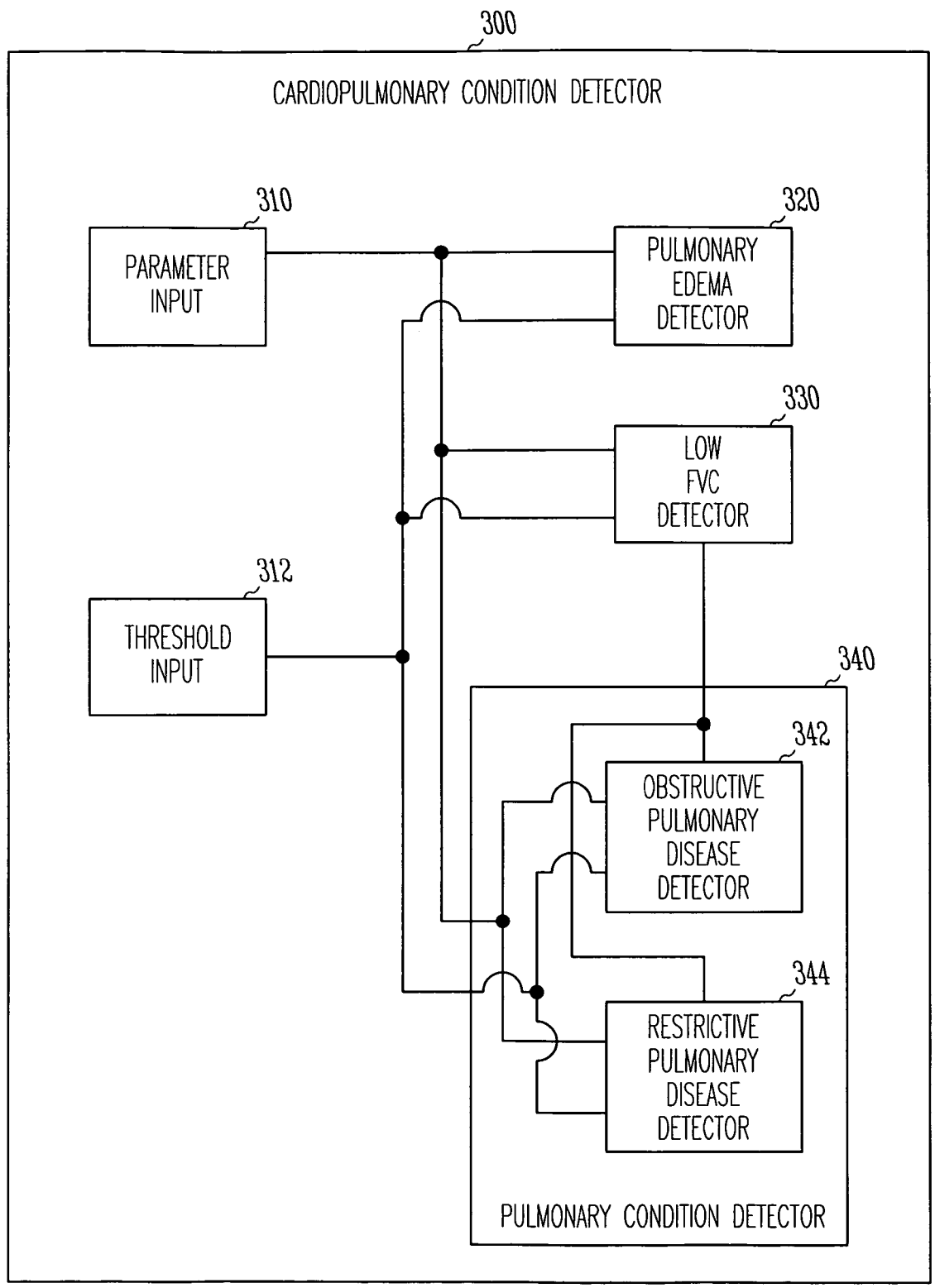
FIG. 3 is a block diagram illustrating one embodiment of a cardiopulmonary condition detector.

FIG. 3 is a block diagram illustrating one embodiment of a cardiopulmonary condition detector 300 for detecting cardiopulmonary conditions. Cardiopulmonary condition detector 300 includes a parameter input 310, a threshold input 312, a pulmonary edema detector 320, a low FVC detector 330, and a pulmonary condition detector 340. Pulmonary condition detector 340 includes an obstructive pulmonary disease detector 342 and a restrictive pulmonary disease detector 344. In one embodiment, cardiopulmonary condition detector 300 includes a computerized circuit executing the automatic detection algorithm discussed above with reference to FIGS. 1A-C.

Parameter input 310 receives parameters indicative of the cardiopulmonary conditions. The parameters are used for the detections performed by cardiopulmonary condition detector 300. In one embodiment, the parameters are produced based on signals sensed by implantable sensors. In another embodiment, the parameters are sensed by a combination of implantable and external sensors.

Threshold input 312 receives threshold values used by detectors 320, 330, 342, and 344. In one embodiment, one or more of these threshold values are programmable and adjusted for each individual patient.

Figure 4:
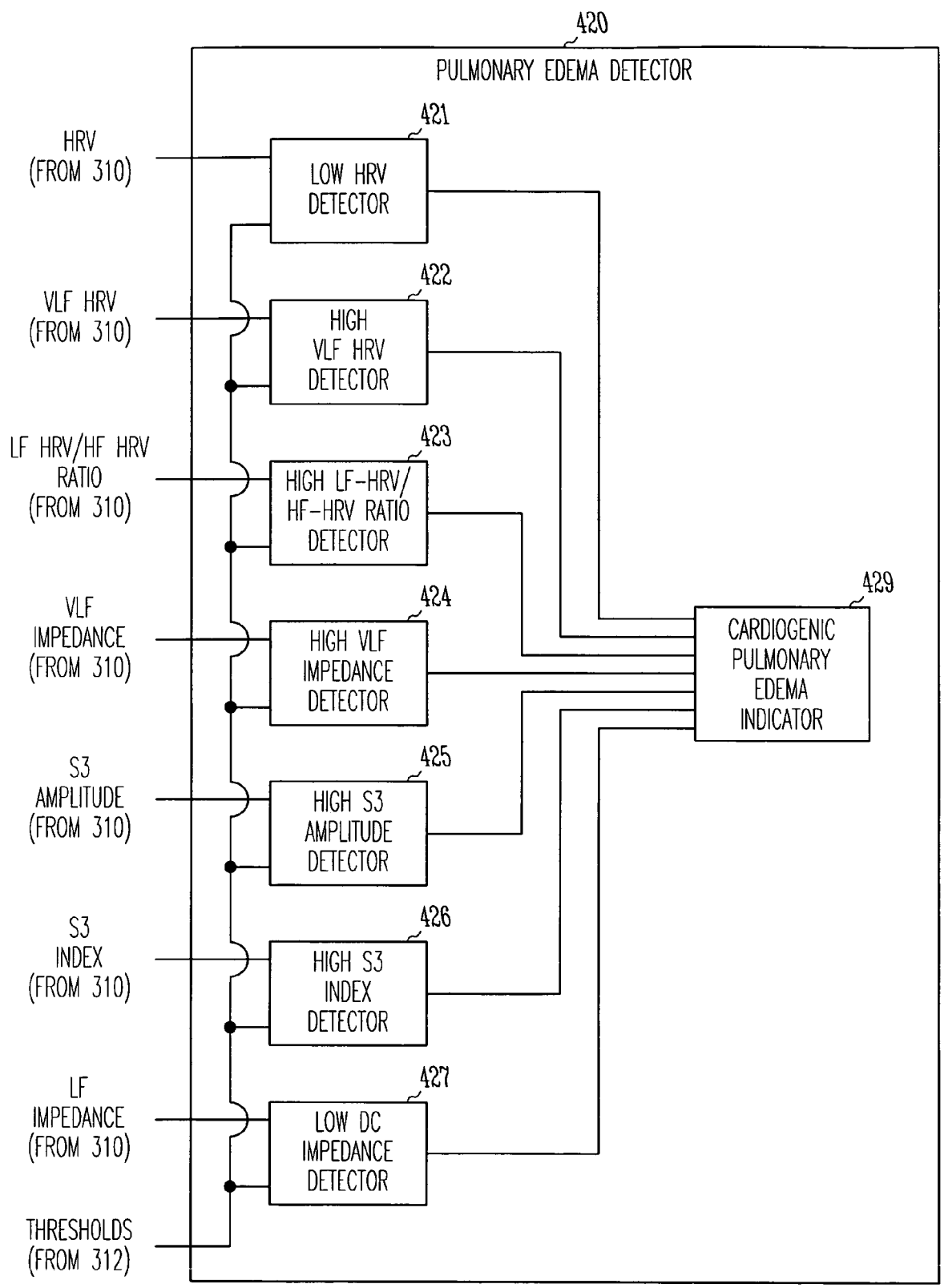
FIG. 4 is a block diagram illustrating one embodiment of a pulmonary edema detector being part of the cardiopulmonary condition detector.

Pulmonary edema detector 320 receives a parameter indicative of pulmonary fluid status and detects cardiogenic pulmonary edema by comparing the signal to a predetermined threshold. FIG. 4 is a block diagram illustrating a circuit of pulmonary edema detector 420 as one embodiment of pulmonary edema detector 320. Pulmonary edema detector 420 includes a low HRV detector 421, a high VLF HRV detector 422, a high LF-HRV/HF-HRV ratio detector 423, a high VLF impedance detector 424, a high S3 amplitude detector 425, a high S3 index detector 426, a low DC impedance detector 427, and a cardiogenic pulmonary edema indicator 429. Low HRV detector 421 includes a comparator having a first input receiving the HRV, a second input representing a predetermined threshold HRV, and an output indicating a detection of cardiogenic pulmonary edema when the HRV is lower than the predetermined threshold HRV or when the decrease in the HRV exceeds the predetermined margin. High VLF HRV detector 422 includes a comparator having a first input receiving the VLF HRV, a second input representing a predetermined threshold VLF HRV, and an output indicating a detection of cardiogenic pulmonary edema when the VLF HRV exceeds the predetermined threshold VLF HRV. High LF-HRV/HF-HRV ratio detector 423 includes a comparator having a first input receiving the LF-HRV/HF-HRV ratio, a second input representing a predetermined threshold ratio, and an output indicating a detection of cardiogenic pulmonary edema when the LF-HRV/HF-HRV ratio exceeds the predetermined threshold ratio. High VLF impedance detector 424 includes a comparator having a first input receiving the VLF impedance signal, a second input representing a predetermined threshold VLF impedance, and an output indicating a detection of cardiogenic pulmonary edema when the VLF impedance exceeds the predetermined threshold VLF impedance. High S3 amplitude detector 425 includes a comparator having a first input receiving the signal indicative of the S3 amplitude, a second input representing a predetermined threshold amplitude, and an output indicating a detection of cardiogenic pulmonary edema when the S3 amplitude exceeds the predetermined threshold amplitude. High S3 index detector 426 includes a comparator having a first input receiving the signal indicative of the S3 index, a second input representing a predetermined threshold index level, and an output indicating a detection of cardiogenic pulmonary edema when the S3 index exceeds the predetermined threshold index level. Low DC impedance detector 427 includes a comparator having a first input receiving the DC impedance signal, a second input representing a predetermined threshold DC impedance, and an output indicating a detection of cardiogenic pulmonary edema when the DC impedance is below the predetermined threshold DC impedance. Cardiogenic pulmonary edema indicator 429 indicates a detection of cardiogenic pulmonary edema based on results of detection by the one or more of detectors 421-427. When two or more of the detectors 421-427 produce results of detection, in one embodiment, cardiogenic pulmonary edema indicator 429 indicates a detection of cardiogenic pulmonary edema if detected by any of detectors cardiogenic. In another embodiment, cardiogenic pulmonary edema indicator 429 indicates a detection of cardiogenic pulmonary edema based on a unanimous or majority voting. In another embodiment, cardiogenic pulmonary edema indicator 429 indicates a detection of cardiogenic pulmonary edema based on a weighted voting, for which predetermined weighing coefficients are assigned to each of the low HRV, high VLF HRV, high LF-HRV/HF-HRV ratio, high VLF impedance, high S3 amplitude, high S3 index, and low DC impedance detections. In one embodiment, pulmonary edema detector 420 is programmable for selective activation of one or more of detectors 421-427. The selection is based on the availability of the parameters (the HRV, VLF HRV, LF-HRV/HF-HRV ratio, VLF impedance, S3 amplitude, S3 index, and DC impedance) and/or a medical judgment on the reliability of detection. In other embodiments, pulmonary edema detector 420 includes any subset of detectors 421-427 and cardiogenic pulmonary edema indicator 429.

Low FVC detector 330 detects a low FVC if pulmonary edema detector 320 does not indicate a detection of cardiogenic pulmonary edema. Low FVC detector 330 includes a comparator having a first input receiving a measured FVC, a second input representing a predetermined threshold FVC, and an output indicating a low FVC when the measured FVC is less than the predetermined threshold FVC.

If low FVC detector 330 indicates a detection of the low FVC, obstructive pulmonary disease detector 342 detects an obstructive pulmonary disease, and restrictive pulmonary disease detector 344 detects a restrictive pulmonary disease, both based on a ratio of the $FEV_N/FVC$ ratio. Obstructive pulmonary disease detector 342 includes a comparator having a first input receiving the $FEV_N/FVC$ ratio, a second input representing a predetermined obstructive pulmonary disease threshold ratio, and an output indicating a detection of obstructive pulmonary disease when the $FEV_N/FVC$ ratio is below the predetermined obstructive pulmonary disease threshold ratio. Restrictive pulmonary disease detector 344 includes a comparator having a first input receiving the $FEV_N/FVC$ ratio, a second input representing a predetermined restrictive pulmonary disease threshold ratio, and an output indicating a detection of restrictive pulmonary disease when the $FEV_N/FVC$ ratio exceeds the predetermined restrictive pulmonary disease threshold ratio.

In one embodiment, cardiopulmonary condition detector 300 includes a command receiver to receive a command triggering the process of detecting cardiogenic pulmonary edema, low FVC, obstructive pulmonary disease, and restrictive pulmonary disease. In one embodiment, the command is entered by a person such as the patient or a physician or other caregiver. In another embodiment, cardiopulmonary condition detector 300 includes a dyspnea detector to produce the command upon a detection of dyspnea. In one embodiment, the dyspnea detector receives a respiratory parameter and an activity level parameter to detect rapid and shallow breath when the patient is at a substantially resting state. In one specific embodiment, the respiratory parameter is the MV impedance sensed by the implantable impedance sensor, and the activity level parameter is derived from the acceleration signal sensed by the implantable accelerometer.

Figure 5:
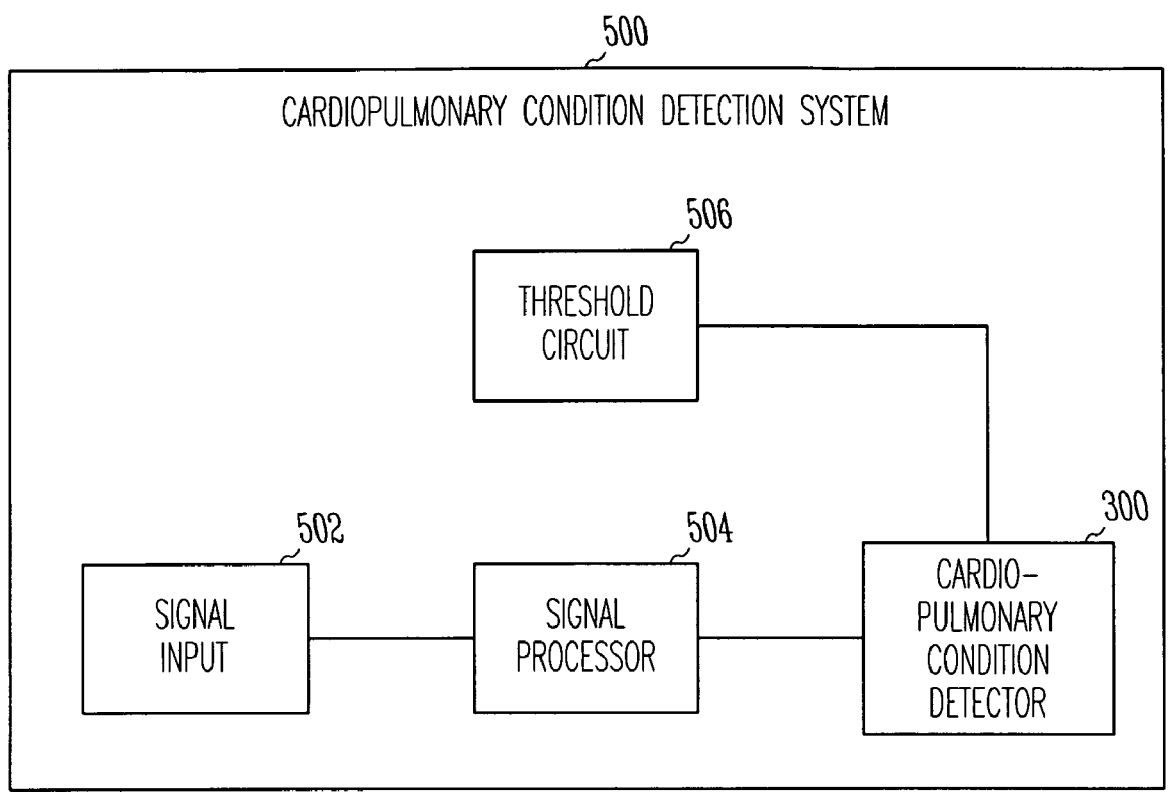
FIG. 5 is a block diagram illustrating one embodiment of a cardiopulmonary condition detection system including the cardiopulmonary condition detector.

FIG. 5 is a block diagram illustrating one embodiment of a cardiopulmonary condition detection system 500 including cardiopulmonary condition detector 300. System 500 includes a signal input 502 that receives signals sensed by one or more sensors and a signal processor 504 that produces the parameters used by cardiopulmonary condition detector 300 based on the received signals. A threshold circuit 506 provides cardiopulmonary condition detector 300 with the thresholds used in the detection of the cardiopulmonary conditions. In one embodiment, signal input 502 receives signals from the implantable sensors. In one specific embodiment, the implantable sensors are included in, and/or connected to, one implantable medical device. In another embodiment, signal input 502 receives signals from both implantable and external sensors.

In one embodiment, system 500 operates by executing an automatic detection algorithm that includes signal processing and parameter production, in addition to the functions of the automatic detection algorithm discussed above with reference to FIGS. 1A-C. System 500 receives signals indicative of cardiopulmonary conditions and detects the cardiopulmonary conditions by executing the automatic detection algorithm using the received signals as inputs. The cardiopulmonary conditions include at least cardiogenic pulmonary edema, obstructive pulmonary disease, and restrictive pulmonary disease.

Signal input 502 includes, but is not limited to, one or more of a cardiac signal input, an impedance signal input, a heart sound signal input, an activity signal input, and a spirometry signal input, depending on which parameters are used for the detections performed by cardiopulmonary condition detector 300. The cardiac signal input receives one or more signals indicative of HRV. In one embodiment, the cardiac signals include one or more electrograms sensed by an implantable medical device having an electrogram sensing circuit. In another embodiment, the cardiac signals include event markers representing cardiac depolarizations detected from the one or more electrograms. The impedance signal input receives one or more impedance signals each indicative of one or more of minute ventilation (lung volume, respiratory pattern), periodic breathing, and pulmonary fluid status. In one embodiment, the one or more impedance signals include a thoracic impedance signal sensed by an implantable impedance sensor. The heart sound input receives one or more heart sound signals indicative of at least S3. In one embodiment, the one or more heart sound signals include an acceleration signal indicative of cardiac mechanical activities sensed by an implantable accelerometer. In another embodiment, the one or more heart sound signals include an acoustic signal sensed by an implantable microphone. The activity signal input receives an activity signal indicative of the patient's gross physical activity level. In one embodiment, the activity signal includes an acceleration signal sensed by an implantable accelerometer. The spirometry signal input receives a spirometry signal indicative of the lung volume sensed by an external spirometer.

Signal processor 504 produces the parameters selected for the detections performed by cardiopulmonary condition detector 300 by processing the signals received by signal input 502. Signal processor 504 includes one or more of an HRV processor, an impedance processor, a heart sound processor, an activity signal processor, and a respiratory signal processor.

The HRV processor produces one or more of the HRV, the VLF HRV, and the LF-HRV/HF-HRV ratio. In one embodiment, the HRV processor includes an HRV measurement module, a VLF HRV generator, an LF HRV generator, an HF HRV generator, and an LF-HRV/HF-HRV ratio calculator. The HRV measurement module measures the HRV based on the one or more electrograms. The VLF HRV generator produces the VLF HRV by extracting the components of the HRV within a VLF frequency band of about 0.0033-0.04 Hz. In one embodiment, the VLF HRV generator includes a filter to produce the VLF HRV as a time-domain signal. In another embodiment, the VLF HRV generator includes a spectral analyzer to produce the VLF HRV as the power distributed in the VLF frequency band. The LF HRV generator produces the LF HRV by extracting the components of the HRV within an LF frequency band of about 0.04-0.15 Hz. In one embodiment, the LF HRV generator includes a filter to produce the LF HRV as a time-domain signal. In another embodiment, the LF HRV generator includes a spectral analyzer to produce the LF HRV as the power distributed in the LF frequency band. The HF HRV generator produces the HF HRV by extracting the components of the HRV within an HF frequency band of about 0.15-0.40 Hz. In one embodiment, the HF HRV generator includes a filter to produce the HF HRV as a time-domain signal. In another embodiment, the HF HRV generator includes a spectral analyzer to produce the HF HRV as the power distributed in the HF frequency band. The LF-HRV/HF-HRV ratio calculator calculates the LF-HRV/HF-HRV ratio by dividing the LF HRV by the HF HRV.

The impedance processor produces the MV impedance, DC impedance, and VLF impedance based on the one or more impedance signals. In one embodiment, the impedance processor includes an MV impedance generator to produce an MV impedance indicative of minute ventilation, a VLF impedance signal generator to produce a VLF impedance suggestive of periodic breathing, and an DC impedance generator to produce an DC impedance indicative of pulmonary fluid status, all from a thoracic impedance signal sensed by the implantable impedance sensor. The VLF impedance generator produces the VLF impedance by extracting the components of the thoracic impedance signal within a VLF frequency band of about 0.0033-0.016 Hz. In one embodiment, the VLF impedance generator includes a filter to produce the VLF impedance as a time-domain signal. In another embodiment, the VLF impedance generator includes a spectral analyzer to produce the VLF impedance as the power distributed in the VLF frequency band. The DC impedance generator produces the DC impedance by extracting the DC (or ultra-low-frequency) components of the thoracic impedance signal. In one embodiment, the VLF impedance generator includes a filter to produce the VLF impedance as a time-domain signal. In another embodiment, the VLF impedance generator includes a spectral analyzer to produce the VLF impedance as the power distributed in the VLF frequency band.

The heart sound processor includes an S3 detector and an S3 analyzer. The S3 detector detects S3 from the one or more heart sound signals. An example of an S3 detector is discussed in U.S. patent application Ser. No. 10/746,853, "METHOD AND APPARATUS FOR THIRD HEART SOUND DETECTION," filed on Dec. 24, 2003, assigned to Cardiac Pacemakers, Inc., which is incorporated herein by reference in its entirety. The S3 analyzer includes one or more of an S3 amplitude measurement module and an S3 index trending module. The S3 amplitude measurement module measures the S3 amplitude based on detected occurrences of S3. In one embodiment, the S3 amplitude measurement module measures amplitudes of a predetermined number of S3 and calculates the S3 amplitude as an average S3 amplitude. In another embodiment, the S3 amplitude measurement module measures amplitudes of S3 over a predetermined time interval and calculates the S3 amplitude as an average S3 amplitude. The S3 index trending module produce the S3 index as a ratio, or an estimate of the ratio, of the number of S3 beats to the number of all heart beats, where the S3 beats are each a heart beat during which an occurrence of S3 is detected. An example of a system trending S3 index is discussed in U.S. patent application Ser. No. 10/746,874, "A THIRD HEART SOUND ACTIVITY INDEX FOR HEART FAILURE MONITORING," filed on Dec. 24, 2003, now U.S. Pat. No. 7,115,096, assigned to Cardiac Pacemakers, Inc., which is incorporated herein by reference in its entirety.

The activity signal processor derives the activity level from the activity signal. In one embodiment, a dual-use sensor senses both the heart sound signal and the activity signal using a single accelerometer. One example of such a dual-use sensor that includes a single accelerometer is discussed in U.S. patent application Ser. No. 10/703,175, "DUAL-USE SENSOR FOR RATE RESPONSIVE PACING AND HEART SOUND MONITORING," filed Nov. 6, 2003, now U.S. Pat. No. 7,248,923, assigned to Cardiac Pacemakers, Inc., which is incorporated herein by reference in its entirety.

The respiratory parameter generator includes an FVC measurement module, an FEV measurement module, and a respiratory ratio calculator. The FVC measurement module measures the FVC, and the FEV measurement module measures the $FEV_N$, both from a respiratory signal being at least one of the MV impedance signal and the spirometry signal. The FEV measurement module is programmable for measuring the $FEV_N$ in a predetermined time (N) referenced to the beginning of an expiratory phase. In one embodiment, the FVC measurement module and the FEV measurement module receive the activity level from the activity signal processor and perform the measurements when the activity level is below a predetermined threshold level representing a substantially resting state. The respiratory ratio calculator calculates the $FEV_N/FVC$ ratio.

Threshold circuit 506 provides the threshold values used by cardiopulmonary condition detector 300. In one embodiment, threshold circuit 506 includes an initial threshold storage circuit, a threshold receiver, and a current threshold register. The initial threshold storage circuit stores a complete set of default values for all thresholds required for the detections performed by cardiopulmonary condition detector 300. The threshold receiver receives threshold values entered for each individual patient. The current threshold register is initialized with the complete set of default values and updated with the threshold values received by the threshold receiver for the individual patient. The threshold values for each individual patient are entered by the user and/or an automated threshold evaluation system. In one embodiment, the automated threshold evaluation system dynamically adjusts one or more thresholds when such a need is detected or otherwise indicated.

Figure 6:
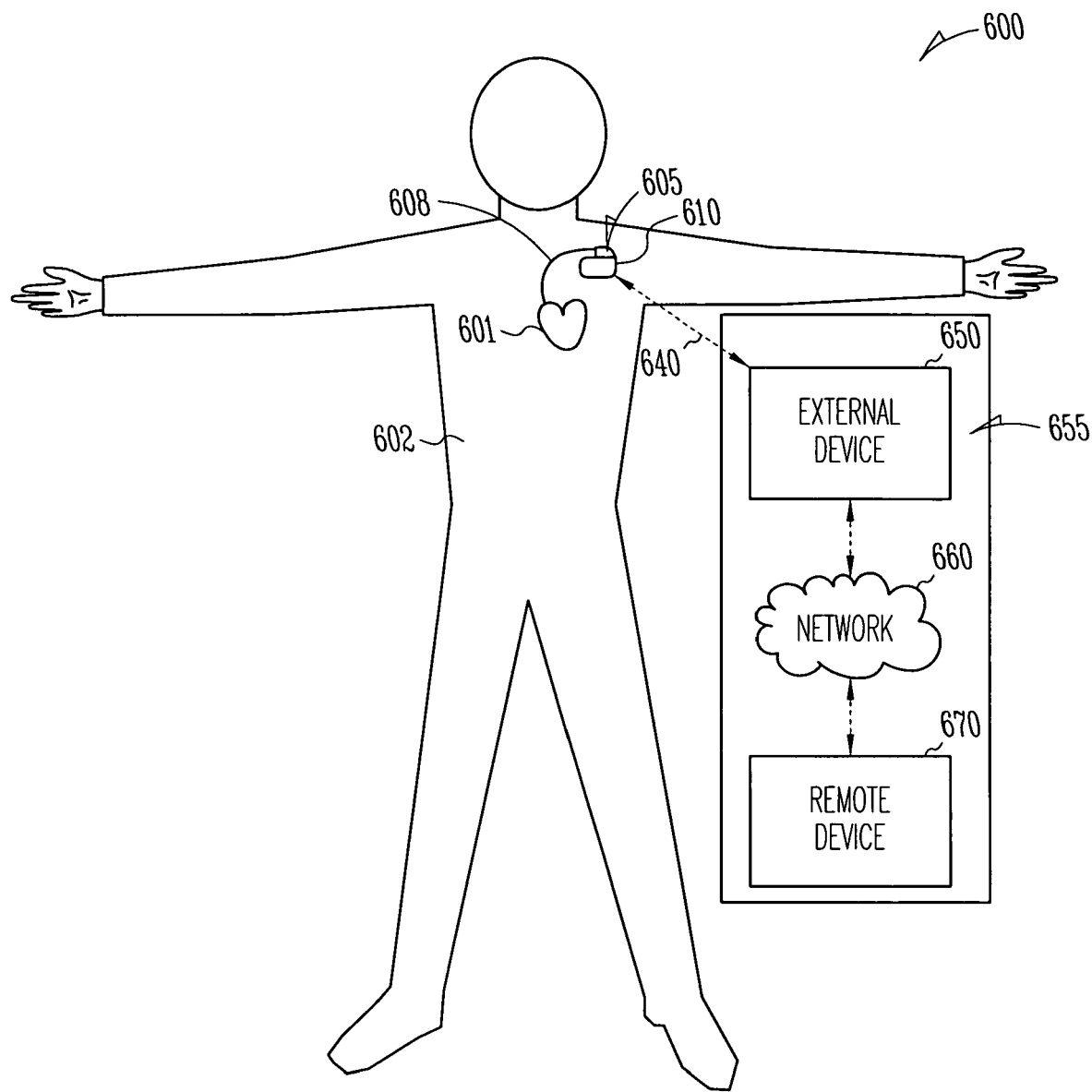
FIG. 6 is an illustration of one embodiment of a system for monitoring heart failure patients with cardiopulmonary comorbidities and portions of the environment in which the system is used.

FIG. 6 is an illustration of one embodiment of a system 600 for monitoring heart failure patients with cardiopulmonary comorbidities and portions of the environment in which system 600 is used. System 600 includes an implantable system 605, an external system 655, and a telemetry link 640 providing for communication between implantable system 605 and external system 655.

Implantable system 605 includes, among other things, implantable medical device 610 and lead system 608. In various embodiments, implantable medical device 610 is an implantable cardiac rhythm management (CRM) device including one or more of a pacemaker, a cardioverter/defibrillator, a cardiac resynchronization therapy (CRT) device, a cardiac remodeling control therapy (RCT) device, a drug delivery device or a drug delivery controller, and a biological therapy device. In one embodiment, implantable medical device 610 includes implantable sensors for sensing the signals used in the detections performed by cardiopulmonary condition detector 300. In another embodiment, implantable medical device 610 and lead system 608 each include one or more of the implantable sensors. As shown in FIG. 6, implantable medical device 610 is implanted in a body 602. Lead system 608 provides connections between implantable medical device 610 and a heart 601. In various embodiments, lead system 608 includes leads for sensing physiological signals and delivering pacing pulses, cardioversion/defibrillation shocks, and/or pharmaceutical or other substances. In one embodiment, at least one implantable sensor is incorporated into a lead of lead system 608 for placement in or about heart 601.

In one embodiment, external system 655 is a patient management system including external device 650, network 660, and remote device 670. External device 650 is within the vicinity of implantable medical device 610 and communicates with implantable medical device 610 bi-directionally via telemetry link 640. Remote device 670 is in a remote location and communicates with external device 1650 bi-directionally via network 660, thus allowing a user to monitor and treat a patient from a distant location. In another embodiment, external system includes a programmer communicating with implantable medical device 610 bi-directionally via telemetry link 640.

System 600 includes cardiopulmonary condition detection system 500 for monitoring the heart failure patients with cardiopulmonary comorbidities. The treatment includes, but is not limited to, one or more of a drug therapy, an electrical therapy (such as pacing, CRT, and RCT), and a biological therapy. The distribution of system 500 in system 600 depends on design and patient management considerations, such as the size and power consumption of each system component and the ability of monitoring the patient in various settings from various locations. In one embodiment, implantable medical device 610 includes the entire system 500. In another embodiment, external system 655 includes the entire system 500. In another embodiment, implantable medical device 610 includes signal input 502, and external system 655 includes signal processor 504, threshold circuit 506, and cardiopulmonary condition detector 300. In another embodiment, implantable medical device 610 includes signal input 502 and signal processor 504, and external system 655 includes threshold circuit 506 and cardiopulmonary condition detector 300. In another embodiment, implantable medical device 610 includes signal input 502 and portions of signal processor 504, and external system 655 includes the other portions of signal processor 504, threshold circuit 506, and cardiopulmonary condition detector 300. In another embodiment, implantable medical device 610 includes signal includes portions of signal input 502 and signal processor 504, and external system 655 includes the other portions of signal input 502 and signal processor 504, threshold circuit 506, and cardiopulmonary condition detector 300. In one specific embodiment, in which external system 655 is the patient management system, remote device 650 includes the cardiopulmonary condition detector 300.

Figure 7:
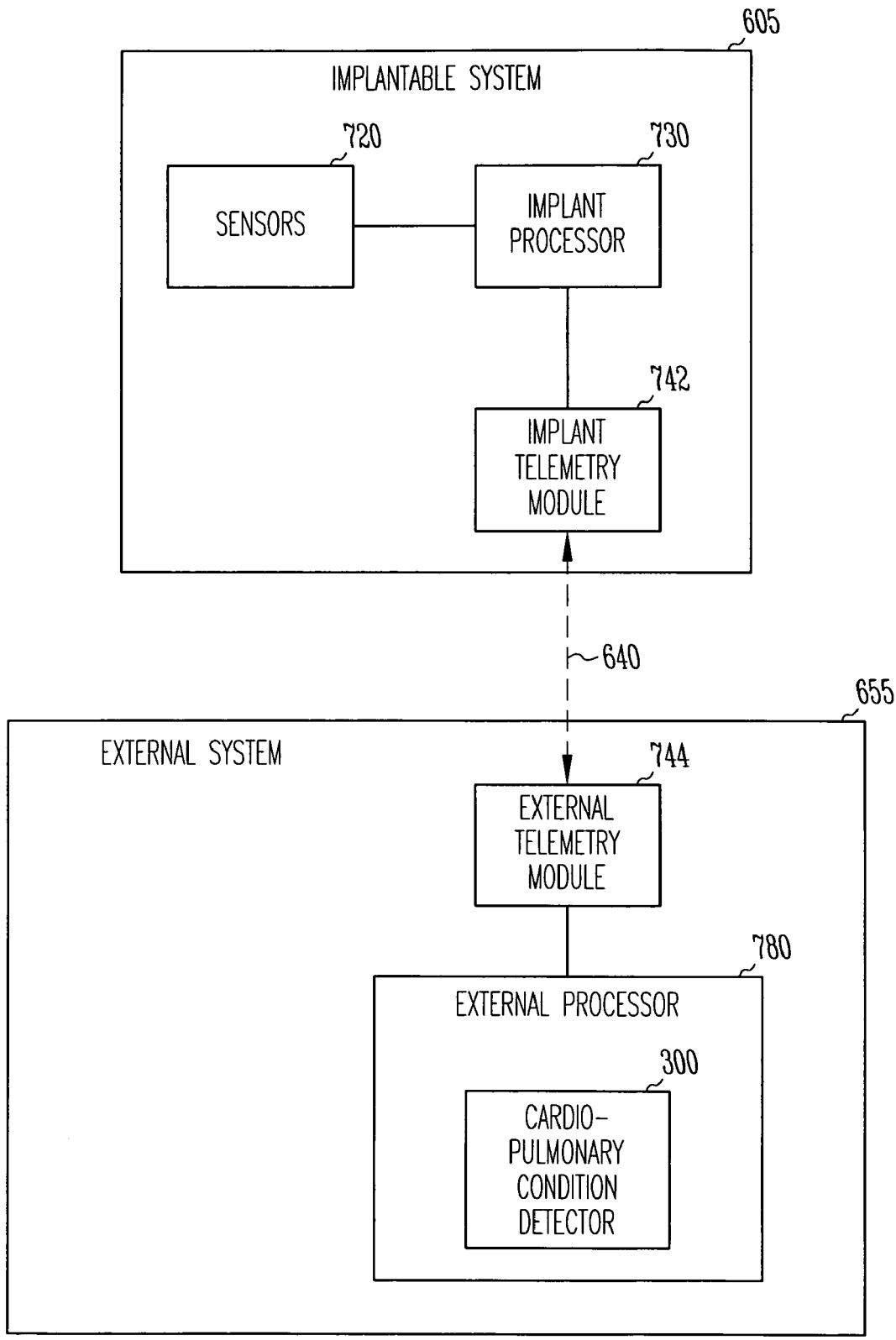
FIG. 7 is a block diagram illustrating one embodiment of a circuit of the system of FIG. 6.

FIG. 7 is a block diagram illustrating one embodiment of a circuit of system 600. The circuit includes various embodiments of system 500.

Implantable system 605 includes sensors 720, implant processor 730, and implant telemetry module 742. In one embodiment, sensors 720, implant processor 730, and implant telemetry module 742 are included in implantable medical device 610. In another embodiment, at least one sensor of sensors 720 is external to implantable medical device 610. External system 780 includes external telemetry module 744 and external processor 780. External processor 780 includes cardiopulmonary condition detector 300. In one embodiment, in which the spirometry signal is used as the respiratory signal, system 600 further includes an external spirometer to sense the spirometry signal. In one embodiment, the external spirometer is electrically connected to external processor 780. In another embodiment, the external spirometer is wirelessly connected to external processor 780 via telemetry.

Sensors 720 include one or more of a sensing circuit, an impedance sensor, a heart sound sensor, and an activity sensor. The sensing circuit senses one or more electrograms indicative of HRV. The impedance sensor senses thoracic impedance. The heart sound sensor detects a heart sound signal indicative of at least S3. In one embodiment, the heart sound sensor includes an accelerometer. In another embodiment, the heart sound sensor includes a microphone. In one embodiment, the heart sound sensor is included in implantable medical device 610. In another embodiment, the heart sound sensor is incorporated into a lead of lead system 608.

The activity sensor senses an activity signal indicative of the patient's gross physical activity level. In one embodiment, the activity sensor includes an accelerometer. In another embodiment, a single accelerometer functions as a dual-use sensor that senses both the heart sound signal and the activity signal.

Implant processor 730 and external processor 780 include system 500. The specific distribution of the component of system 500 in implant processor 730 and external processor 780 depends on specific design and patient management considerations. In one embodiment, implant processor 730 includes signal input 502 and signal processor 504, and external processor 780 includes threshold circuit 506 and cardiopulmonary condition detector 300. In another embodiment, implant processor 730 includes signal input 502, and external processor 780 includes signal processor 504, threshold circuit 506, and cardiopulmonary condition detector 300. In another embodiment, implant processor 730 includes signal input 502 and portions of signal processor 504, and external processor 780 includes the other portions of signal processor 504, threshold circuit 506, and cardiopulmonary condition detector 300. In another embodiment, implant processor 730 includes portions of signal input 502 and signal processor 504, and external processor 780 includes the other portions of signal input 502 and signal processor 504, threshold circuit 506, and cardiopulmonary condition detector 300. In one specific embodiment in which both implant processor 730 and external processor 780 both include portions of signal processor 504, implant processor 730 includes one or more of the HRV measurement module, the impedance processor, the heart sound processor, and the activity signal processor; external processor includes one or more of the S3 analyzer and the respiratory parameter generator.

Implant telemetry module 742 and external telemetry module 744 supports telemetry link 640. Telemetry link 640 is a wireless bi-directional data transmission link. In one embodiment, telemetry link 640 is an inductive couple formed when two coils—one connected to implant telemetry module 742 and the other connected to external telemetry module 744—are placed near each other. In this embodiment, the patient or the user places the coil connected to external device 650 on body 602 over implantable medical device 610. In another embodiment, telemetry link 640 is a far-field radio-frequency telemetry link allowing implantable medical device 610 and external device 650 to communicate over a telemetry range that is at least ten feet. In one embodiment, implant telemetry module 742 transmits one or more signals and/or parameters indicative of cardiopulmonary conditions, and external telemetry module 744 receives these signals and/or parameters.

Figure 8:
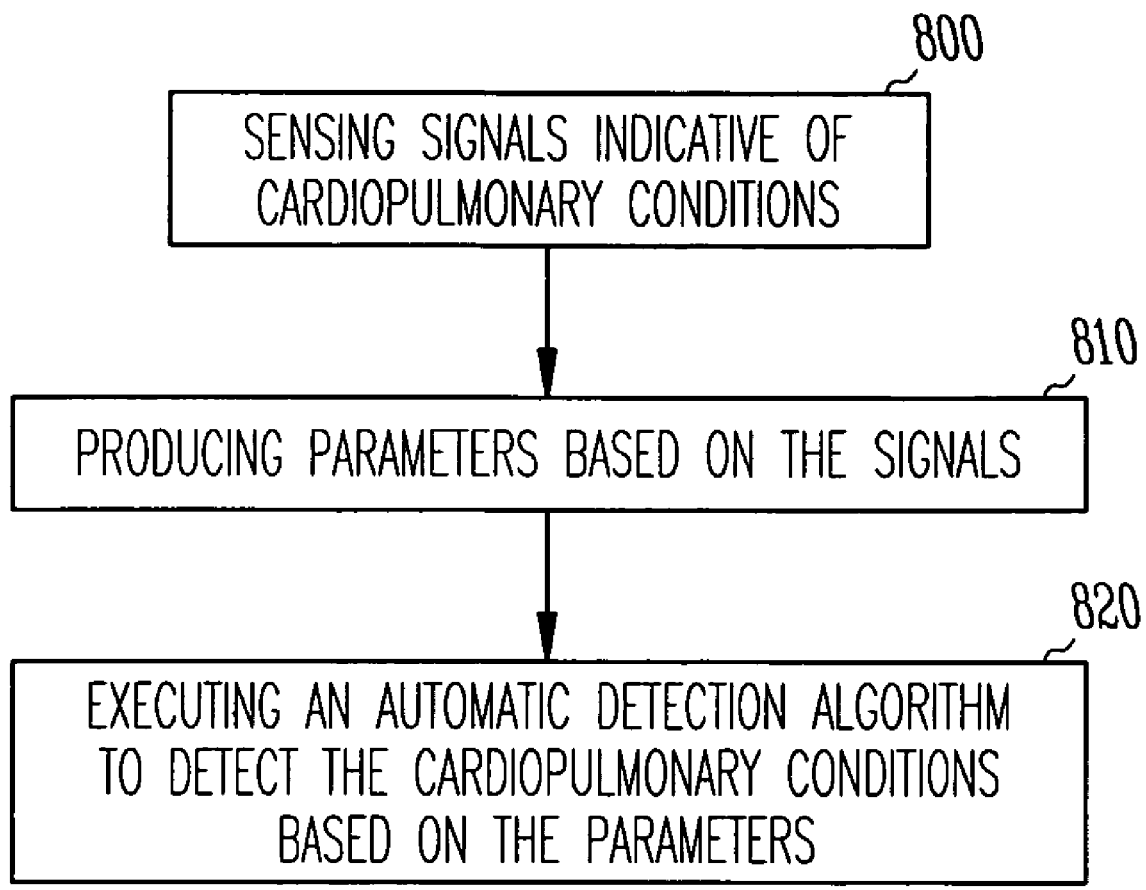
FIG. 8 is a flow chart illustrating one embodiment of a method for monitoring heart failure patients with cardiopulmonary comorbidities.

FIG. 8 is a flow chart illustrating one embodiment of a method for monitoring heart failure patients with cardiopulmonary comorbidities. In one embodiment, the method is performed by system 600.

Signals indicative of a plurality of cardiopulmonary conditions are sensed at 800. Based on the sensed signals, parameters indicative of the plurality of cardiopulmonary conditions are produced at 810. An automatic detection algorithm is executed to detect the plurality of cardiopulmonary conditions based on the parameters at 820. The plurality of cardiopulmonary conditions includes at least cardiogenic pulmonary edema, obstructive pulmonary disease, and restrictive pulmonary disease. In one embodiment, the automatic detection algorithm performs the method discussed above with reference to FIGS. 1A-C.

In one specific embodiment using system 600, sensors 720 senses the signals at 800. Implant processor 730 and/or external processor 780 produce the parameters at 810. Cardiopulmonary condition detector 300 executes the automatic detection algorithm to detect cardiogenic pulmonary edema, obstructive pulmonary disease, and restrictive pulmonary disease based on the parameters.

It is to be understood that the above detailed description is intended to be illustrative, and not restrictive. For example, the method for detecting the cardiopulmonary conditions including cardiogenic pulmonary edema, obstructive pulmonary disease, and restrictive pulmonary disease may be implemented without using implantable sensors. The method of using a combination of implantable and external systems for differential diagnostic purposes is not limited to diagnosis of cardiopulmonary conditions. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. A system, comprising:
    an implantable medical device including:
        a plurality of sensors adapted to sense a plurality of signals indicative of a plurality of cardiopulmonary conditions including cardiogenic pulmonary edema, obstructive pulmonary disease, and restrictive pulmonary disease;
        an implant processor, coupled to the plurality of sensors, to process the plurality of signals; and
        an implant telemetry module, coupled to the implant processor, to transmit the processed plurality of signals; and
    an external system communicatively coupled to the implantable medical device via telemetry, the external system including:
        an external telemetry module to receive the processed plurality of signals; and
        an external processor coupled to the external telemetry module, the external processor including a cardiopulmonary condition detector adapted to detect dyspnea based on at least one or more signals of the processed plurality of signals and detect the plurality of cardiopulmonary conditions based on the processed plurality of signals after the dyspnea is detected, the cardiopulmonary condition detector including at least a cardiogenic pulmonary edema detector, an obstructive pulmonary disease detector, and a restrictive pulmonary disease detector.

2. The system of claim 1, wherein the implantable medical device comprises an implantable cardiac rhythm management (CRM) device.

3. The system of claim 1, wherein the external system comprises a programmer.

4. The system of claim 1, wherein the external system comprises a patient management system including:
    an external device communicatively coupled to the implantable medical device;
    a telecommunication network coupled to the external device; and
    a remote device, coupled to the telecommunication network, to allow access to the implantable medical device from a remote location.

5. The system of claim 4, wherein the remote device comprises the cardiopulmonary condition detector.

6. The system of claim 5, wherein the plurality of sensors comprise a sensing circuit to sense one or more electrograms, and the implant processor comprises a heart rate variability (HRV) processor adapted to measure an HRV from the one or more electrograms and adapted to produce one or more parameters indicative of cardiogenic pulmonary edema based on the HRV.

7. The system of claim 1, wherein the plurality of sensors comprise an impedance sensor to sense a thoracic impedance, and the implant processor comprises an impedance processor adapted to produce one or more parameters indicative of cardiogenic pulmonary edema based on the thoracic impedance.

8. The system of claim 1, wherein the external processor further comprises a forced vital capacity (FVC) measurement module adapted to measure an FVC parameter from a signal of the processed plurality of signals and a forced expiratory volume (FEV) measurement module adapted to measure an FEV parameter from the signal of the processed plurality of signals, and the obstructive pulmonary disease detector is adapted to detect an obstructive pulmonary disease based on the FVC parameter and the FEV parameter, and the restrictive pulmonary disease detector is adapted to detect a restrictive pulmonary disease based on the FVC parameter and the FEV parameter.

9. The system of claim 8, wherein the cardiopulmonary condition detector further comprises a low FVC detector, coupled to the pulmonary edema detector, to detect a low FVC when the FVC parameter is less than a predetermined threshold FVC parameter value if the cardiogenic pulmonary edema is not detected, and wherein the obstructive pulmonary disease detector is adapted to detect the obstructive pulmonary disease if the low FVC is detected, and the restrictive pulmonary disease detector is adapted to detect the restrictive pulmonary disease if the low FVC is detected.

10. The system of claim 8, wherein the plurality of sensors comprise an impedance sensor to sense an impedance signal indicative of minute ventilation, the
    FVC measurement module is adapted to measure the FVC parameter from the impedance signal, and
    FEV measurement module is adapted to measure the FEV parameter from the impedance signal.

11. The system of claim 10, wherein the plurality of sensors further comprise an activity sensor to sense an activity signal indicative of a physical activity level, and wherein:
    the FVC measurement module is adapted to measure the FVC parameter from the MV impedance signal when the activity signal indicates a substantially resting state; and
    the FEV measurement module is adapted to measure the FEV parameter from the MV impedance signal when the activity signal indicates a substantially resting state.

12. A system, comprising:
    an implantable medical device including:
        a plurality of sensors adapted to sense a plurality of signals indicative of a plurality of cardiopulmonary conditions, the plurality of sensors including a heart sound sensor to sense a heart sound signal indicative of at least third heart sounds (S3);
        an implant processor, coupled to the plurality of sensors, to process the plurality of signals, the implant processor including an S3 processor adapted to detect occurrences of S3 and adapted to produce one or more parameters indicative of cardiogenic pulmonary edema based on the detected occurrences of S3; and
        an implant telemetry module, coupled to the implant processor, to transmit the processed plurality of signals; and
    an external system communicatively coupled to the implantable medical device via telemetry, the external system including:
        an external telemetry module to receive the processed plurality of signals; and
        an external processor coupled to the external telemetry module, the external processor including a cardiopulmonary condition detector adapted to detect the plurality of cardiopulmonary conditions based on the processed plurality of signals, the cardiopulmonary condition detector including at least a cardiogenic pulmonary edema detector, an obstructive pulmonary disease detector, and a restrictive pulmonary disease detector, wherein the cardiogenic pulmonary edema detector is adapted to detect the cardiogenic pulmonary edema based on the one or more parameters indicative of cardiogenic pulmonary edema.

13. The system of claim 12, wherein the external processor is adapted to measure a forced vital capacity (FVC) parameter and a forced expiratory volume (FEV) parameter from a signal of the processed plurality of signals, the obstructive pulmonary disease detector is adapted to detect an obstructive pulmonary disease based on the FVC parameter and the FEV parameter, and the restrictive pulmonary disease detector is adapted to detect a restrictive pulmonary disease based on the FVC parameter and the FEV parameter.

14. A system, comprising:
    an implantable medical device including:
        a first sensor adapted to sense a first signal indicative of cardiogenic pulmonary edema;
        an implant processor, coupled to the sensor, to process the first signal; and
        an implant telemetry module, coupled to the implant processor, to transmit the processed first signal;
    an external spirometer adapted to sense a spirometry signal indicative of lung volume; and
    an external system adapted to be coupled to the external spirometer and communicatively coupled to the implantable medical device via telemetry, the external system including:
        an external telemetry module to receive the processed first signal; and
        an external processor coupled to the external telemetry module, the external processor including:
            a forced vital capacity (FVC) measurement module adapted to measure an FVC parameter from the spirometry signal;
            a forced expiratory volume (FEV) measurement module adapted to measure an FEV parameter from the spirometry signal;
            a cardiogenic pulmonary edema detector adapted to detect cardiogenic pulmonary edema based on the processed first signal;
            an obstructive pulmonary disease detector adapted to detect an obstructive pulmonary disease based on the FVC parameter and the FEV parameter; and
            and a restrictive pulmonary disease detector adapted to detect a restrictive pulmonary disease based on the FVC parameter and the FEV parameter.

15. The system of claim 14, wherein the first sensor comprises a sensing circuit to sense one or more electrograms, an impedance sensor to sense a thoracic impedance, or a heart sound sensor to sense a heart sound signal indicative of at least third heart sounds (S3).

16. A system, comprising:
    an implantable medical device including:

means for sensing a plurality of signals indicative of a plurality of cardiopulmonary conditions, the plurality of signals including one or more signals indicative of dyspnea;
means for processing the plurality of signals; and
means for transmitting the processed plurality of signals; and
an external system adapted to be communicatively coupled to the implantable medical device via telemetry, the external system including:
means for receiving the processed plurality of signals; and
means for detecting the dyspnea using the processed one or more signals indicative of dyspnea and for detecting at least cardiogenic pulmonary edema, obstructive pulmonary disease, and restrictive pulmonary disease using the processed plurality of signals after the dyspnea is detected.

17. The system of claim 16, wherein the means for sensing comprises means for sensing one or more electrograms indicative of heart rate variability (HRV), and the means for detecting the plurality of cardiopulmonary conditions comprises means for detecting the cardiogenic pulmonary edema using at least one or more HRV parameters produced using the one or more electrograms.

18. The system of claim 16, wherein the means for sensing comprises means for sensing a heart sound signal indicative of at least third heart sounds (S3), and the means for detecting the plurality of cardiopulmonary conditions comprises means for detecting the cardiogenic pulmonary edema using at least one or more heart sound parameters produced using the heart sound signal.

19. The system of claim 16, wherein the means for sensing comprises means for sensing a thoracic impedance, and the means for detecting the plurality of cardiopulmonary conditions comprises means for detecting the cardiogenic pulmonary edema using at least one or more impedance parameters produced using the thoracic impedance.

20. The system of claim 19, wherein the means for detecting the plurality of cardiopulmonary conditions further comprises:
means for producing a minute ventilation (MV) impedance signal based on the thoracic impedance, the MV impedance signal indicative of minute ventilation; and
means for measuring a force vital capacity (FVC) parameter and a forced expiratory volume (FEV) parameter from the MV impedance signal.

* * * * *